(12) United States Patent
Teo et al.

(10) Patent No.: US 10,799,458 B2
(45) Date of Patent: *Oct. 13, 2020

(54) METHOD AND SYSTEM FOR PRODUCING HIGH PURITY VANCOMYCIN HYDROCHLORIDE

(71) Applicant: ZHEJIANG MEDICINE CO., LTD, Shaoxing (CN)

(72) Inventors: Choon Teo, Hangahou Zhejliang (CN); Xinqiang Sun, Xinchang Zhejiang (CN); Xiaoyong Wang, Zhejiang (CN)

(73) Assignee: ZHEJIANG MEDICINE CO., LTD, Binhai New Area Shaoxing (CN)

( * ) Notice: Subject to any disclaimer, the term of this patent is extended or adjusted under 35 U.S.C. 154(b) by 0 days.

This patent is subject to a terminal disclaimer.

(21) Appl. No.: 15/241,863

(22) Filed: Aug. 19, 2016

(65) Prior Publication Data

US 2017/0042817 A1 Feb. 16, 2017

Related U.S. Application Data

(63) Continuation of application No. 14/024,131, filed on Sep. 11, 2013, now Pat. No. 9,428,291.

(30) Foreign Application Priority Data

Mar. 15, 2013 (CN) .......................... 2013 1 0085761

(51) Int. Cl.
| | | |
|---|---|---|
| *A61K 9/16* | (2006.01) | |
| *A61J 3/07* | (2006.01) | |
| *A61K 38/14* | (2006.01) | |
| *B01D 1/18* | (2006.01) | |
| *B65B 31/02* | (2006.01) | |
| *A61J 3/02* | (2006.01) | |
| *B01D 61/02* | (2006.01) | |
| *B65B 1/04* | (2006.01) | |
| *B65B 7/16* | (2006.01) | |
| *B65B 31/00* | (2006.01) | |
| *B65B 63/08* | (2006.01) | |

(52) U.S. Cl.
CPC .............. *A61K 9/1623* (2013.01); *A61J 3/02* (2013.01); *A61K 9/1694* (2013.01); *A61K 38/14* (2013.01); *B01D 1/18* (2013.01); *B01D 61/025* (2013.01); *B01D 61/027* (2013.01); *B65B 1/04* (2013.01); *B65B 7/161* (2013.01); *B65B 31/00* (2013.01); *B65B 31/028* (2013.01); *B65B 63/08* (2013.01)

(58) Field of Classification Search
CPC ....... A61K 9/1694; A61K 9/1682; B01D 1/18
See application file for complete search history.

(56) References Cited

U.S. PATENT DOCUMENTS

| | | |
|---|---|---|
| 3,067,099 A | 12/1962 | McCormick et al. |
| 4,440,753 A | 4/1984 | McCormick et al. |
| 4,540,602 A | 9/1985 | Motoyama et al. |
| 4,831,015 A | 5/1989 | Waite |
| 4,868,285 A | 9/1989 | Wall |
| 5,458,135 A | 10/1995 | Patton et al. |
| 5,607,915 A | 3/1997 | Patton |
| 5,756,552 A | 5/1998 | Takeuchi et al. |
| 5,785,049 A | 7/1998 | Smith et al. |
| 5,794,647 A | 8/1998 | Denmark et al. |
| 5,853,720 A | 12/1998 | Pflaum et al. |
| 6,001,800 A | 12/1999 | Mehta et al. |
| 6,051,256 A | 4/2000 | Platz et al. |
| 6,253,463 B1 | 7/2001 | Hansen |
| 6,308,434 B1 | 10/2001 | Chickering, III et al. |
| 6,372,258 B1 | 4/2002 | Platz et al. |
| 6,423,344 B1 | 7/2002 | Platz et al. |
| 6,433,344 B1 | 8/2002 | Salisbury et al. |
| 6,479,049 B1 | 11/2002 | Platz et al. |
| 6,518,239 B1 | 2/2003 | Kuo et al. |
| 6,582,728 B1 | 6/2003 | Platz et al. |
| 6,592,904 B2 | 7/2003 | Platz et al. |
| 6,645,528 B1 | 11/2003 | Straub et al. |
| 6,673,335 B1 | 1/2004 | Platz et al. |
| 6,730,923 B1 | 5/2004 | May et al. |
| 6,763,607 B2 | 7/2004 | Beyerinck et al. |

(Continued)

FOREIGN PATENT DOCUMENTS

| | | |
|---|---|---|
| CN | 1415758 A | 5/2003 |
| CN | 101440127 B | 10/2012 |

(Continued)

OTHER PUBLICATIONS

Moran, et al., "Studies of the Crystallization of Amorphous Trehalose Using Simultaneous Gravimetric Vapor Sorption/Near IR (GVS/NIR) and "Modulated" GVS/NIR," AAPS PharmSciTech, vol. 10, No. 1, pp. 297-302 (Mar. 2009).

(Continued)

*Primary Examiner* — Kyle A Purdy
(74) *Attorney, Agent, or Firm* — Mayer Brown LLP

(57) ABSTRACT

A method is provided for preparing spray dried powder containing vancomycin hydrochloride. The method comprises providing a vancomycin hydrochloride solution with a chromatographic purity of at least 95%, adding an excipient to the vancomycin hydrochloride solution to form a mixture solution of the vancomycin hydrochloride solution and the excipient, concentrating the mixed solution of the vancomycin hydrochloride solution and the excipient to form a 20% to 30% vancomycin concentrate, filtering the vancomycin concentrate to form a final filtrate, and spray drying the final filtrate to form a spray dried vancomycin hydrochloride powder with EP impurity B level of not more than 1.5%.

17 Claims, 6 Drawing Sheets

(56) References Cited

U.S. PATENT DOCUMENTS

| | | |
|---|---|---|
| 6,797,258 B2 | 9/2004 | Platz et al. |
| 6,921,527 B2 | 7/2005 | Platz et al. |
| 6,932,983 B1 | 8/2005 | Straub et al. |
| 6,973,741 B2 | 12/2005 | Beyerinck et al. |
| 7,018,804 B1 | 3/2006 | Zeigler |
| 7,060,285 B2 | 6/2006 | Muller |
| 7,108,865 B2 | 9/2006 | Curatolo et al. |
| 7,138,141 B2 | 11/2006 | Platz et al. |
| 7,147,869 B2 | 12/2006 | Dietrich et al. |
| 7,148,211 B2 | 12/2006 | Mazess et al. |
| 7,414,114 B2 | 8/2008 | Singh et al. |
| 7,482,024 B2 | 1/2009 | Kuo et al. |
| 7,550,158 B2 | 6/2009 | Appel et al. |
| 7,700,130 B2 | 4/2010 | Truong-Le et al. |
| 7,736,672 B2 | 6/2010 | Ray et al. |
| 7,780,988 B2 | 8/2010 | Beyerinck et al. |
| 8,026,286 B2 | 9/2011 | Curatolo et al. |
| 8,039,619 B2 | 10/2011 | Sundaram et al. |
| 8,125,333 B2 | 2/2012 | Ressler et al. |
| 2001/0018072 A1 | 8/2001 | Unger |
| 2002/0111311 A1 | 8/2002 | Govardhan et al. |
| 2002/0155183 A1 | 10/2002 | Bathurst et al. |
| 2002/0197212 A1 | 12/2002 | Osbakken et al. |
| 2003/0045484 A1 | 3/2003 | Keith et al. |
| 2003/0124191 A1 | 7/2003 | Besse et al. |
| 2003/0155531 A1 | 8/2003 | Clark et al. |
| 2005/0026813 A1 | 2/2005 | Olstein et al. |
| 2005/0250705 A1 | 11/2005 | Bassarab et al. |
| 2006/0093677 A1 | 5/2006 | Chickering, III et al. |
| 2006/0228251 A1 | 10/2006 | Schneberger et al. |
| 2006/0292081 A1 | 12/2006 | Morton et al. |
| 2007/0026083 A1 | 2/2007 | Doney |
| 2007/0087980 A1 | 4/2007 | Suzuki et al. |
| 2007/0178165 A1 | 8/2007 | Altreuter et al. |
| 2008/0096831 A1 | 4/2008 | Sadatrezaei et al. |
| 2008/0181962 A1 | 7/2008 | Brzeczko et al. |
| 2008/0188403 A1 | 8/2008 | Chaudhary |
| 2008/0194820 A1 | 8/2008 | Sundaram et al. |
| 2008/0199353 A1 | 8/2008 | Mlodzinski et al. |
| 2008/0213366 A1 | 9/2008 | Gowan, Jr. et al. |
| 2009/0098200 A1 | 4/2009 | Temtsin Krazy et al. |
| 2009/0221471 A1 | 9/2009 | Greenwald et al. |
| 2010/0028440 A1 | 2/2010 | Dobry et al. |
| 2010/0041589 A2 | 2/2010 | Keith et al. |
| 2010/0049257 A1 | 2/2010 | Parker |
| 2010/0049322 A1 | 2/2010 | McKay |
| 2010/0056784 A1 | 3/2010 | Lopez et al. |
| 2010/0057910 A1 | 3/2010 | Kaplinger et al. |
| 2010/0116294 A1 | 5/2010 | Turok et al. |
| 2010/0305054 A1 | 12/2010 | Bowman et al. |
| 2011/0124551 A1 | 5/2011 | Palepu et al. |
| 2011/0207658 A1 | 8/2011 | Kelleher et al. |
| 2011/0251125 A1 | 10/2011 | Bay et al. |
| 2011/0257197 A1 | 10/2011 | Xu |
| 2012/0189666 A1 | 7/2012 | Dhoot et al. |
| 2013/0009330 A1 | 1/2013 | Fragale et al. |
| 2014/0079777 A1 | 3/2014 | Lord et al. |

FOREIGN PATENT DOCUMENTS

| | | |
|---|---|---|
| CN | 101456903 B | 6/2013 |
| EP | 0386951 A2 | 9/1990 |
| JP | 11080022 A | 3/1999 |
| WO | 01/47542 A1 | 7/2001 |
| WO | 2006055950 A1 | 5/2006 |
| WO | 2010082726 A2 | 7/2010 |
| WO | 2010092395 A1 | 8/2010 |

OTHER PUBLICATIONS

Kovalcik, et al., "The Stability of Cyclophosohamide in Lyophilized Caked. Part I. Mannitol, Lactose, and Sodium Bicarbonate as Excipients," PDA J Pharm Sci and Tech, 42(1), pp. 29-37 (1988).

Akade, et al., "Influence of Polyethylene Glycol 6000 and Mannitol on the in-Vitro Dissolution Properties of Nitrofurantoin by the Dispersion Technique," Die Pharmazie, 41, pp. 849-851 (1986).

ChargePoint Technology, Chargepoint(R) and ChargePoint(R) Excel (2010).

http://www.nironic.com/harma_systems/pharmaceutical_spray_dryer: Pharmaceutical Spray Dryers PSD, cGMP Solvent Based, Printed on Oct. 12, 2010.

Maury, et al., "Effects of Process Variables on the Powder Yield of Spray-Dried Trehalose on a Laboratory Spray-Dryer," European Journal of Pharmaceutics and Biopharmaceutics, 59, pp: 565-573 (2005).

http://www.thechargepoint.comllcontainment-technology/split-butterfly-valve.phuse; Containment Technology—Introduction to Split Butterfly Valves, Containment Theory.

Ghassempour, et al., "Vancomycin Degradation Products as Potential Chiral Selectors in Enantiomeric Separation of Racemic Compounds," Journal of Chromatography A, 1191,182-187 (2008).

Naini et al, "Physicocehmical Stability of Crystalline Sugars and Their Spray-Dried Forms: Dependence upon Relative Humidity and Suitability for Use in Power Inhalers," Drug Development and Industrial Pharmacy, 24(10), pp. 895-909 (1998).

Moran, et al., "Adjusting and Understanding the Properties of Crystallisation Behaviour of Amorphous Trehalose as a Function of Spray Drying Feed Concentration," International Journal Pharmaceutics, 343, pp. 12-17 (2007).

Nieto, et al., "Physicochmeical Properties of Vancomycin and lodovancomycin and their Complexes with Diacetyl-L-lysyl-D-alanyl-D-alanine," Biochem, J., 123, pp. 773-787 (1971).

Pathways of desamidovancomycin

METHOD AND SYSTEM FOR PRODUCING HIGH PURITY VANCOMYCIN HYDROCHLORIDE

CROSS-REFERENCE TO RELATED APPLICATION

This application is a continuation of U.S. patent application Ser. No. 14/024,131, filed on Sep. 11, 2013, which is based on and claims priority under 35 U.S.C. 119 from Chinese Patent Application No. 201310085761.7, filed Mar. 15, 2013, titled "Spray Dry Powder and Industrial Preparation of Vancomycin Hydrochloride," which are incorporated herein by reference in their entirety to the full extent permitted by law.

FIELD OF THE DISCLOSURE

The present disclosure relates to a system and a method for producing high purity vancomycin hydrochloride.

BACKGROUND OF THE DISCLOSURE

Vancomycin hydrochloride is an amphoteric glycopeptide antibiotic produced by fermentation of the microorganism *Nocardia orientalis* (or *Amycolatopsis orientalis*) under controlled conditions, which has a molecular formula $C_{66}H_{75}Cl_2N_9O_{24}$·HCl and a molecular weight of 1.486. Commercial distribution of vancomycin hydrochloride began at the end of 1950s and its chloride form has been used clinically ever since. Lyophilized vancomycin hydrochloride is a white or almost white powder. It is hygroscopic, freely soluble in water, and slightly soluble in alcohol. When mixed with water (5%, w/w), vancomycin hydrochloride has a pH between 2.5 and 4:5.

Vancomycin hydrochloride acts by binding the C-terminal D-Ala-D-Ala peptides, which inhibits the synthesis of cell walls and also changes the permeability of cell membranes as well as synthesis of RNA. Vancomycin hydrochloride is particularly used for the initial treatment of serious or severe infections caused by staphylococci resistant to β-lactam antibiotics as well as in patients who are penicillin-sensitive or do not respond to penicillin or cephalosporine. Vancomycin hydrochloride is commercially available in oral (solution and capsules/pulvules) and parenteral (sterile intravenous solution in vials) forms.

Vancomycin hydrochloride, alone or in combination with other aminoglycosides, is useful in treating staphylococcal, streptococcal, enterococcal or diphtherial endocarditis. An indication of oral vancomycin therapy includes the treatment of pseudomembranous colitis caused by staphylococci when it is unresponsive to vancomycin for injection. Vancomycin for injection may be applicable to all of the other indications.

A vancomycin molecule is composed of two basic structures, including a saccharide group, α-o-vancosamine-β-o-glucosyl, and a heptapeptide backbone. The structure of vancomycin determines its instability and the ease with which it may be degraded under acidic conditions, alkaline conditions and/or high temperature conditions. Normally, degradation products have no biological activity, so side effects may be reduced when impurity levels are significantly reduced.

Desvancosaminyl vancomycin and aglucovancomycin are degradation products that result from the loss of the disaccharide moiety and the vancosamine sugar, respectively, under acidic and high temperature conditions. Vancomycin can be degraded into another degradation product, desamidovancornycin, by hydrolytic loss of ammonia in weak acid conditions. Desamidovancomycin exists in two isomeric forms as shown in FIGS. 1 and 2. The forming mechanism of Desamidovancomycin has been described in publications, such as, for example, "Vancomycin degradation products as potential chiral selectors in enantiomeric separation of racemic compounds," by Alireza Ghassempour, Journal of Chromatography A, 1191(2008) 182-187. In this publication, the authors deduced that there are two pathways for vancomycin to succinimide and its conversion to desamidovancomycin, as described in FIG. 3.

Industrial methods for preparing vancomycin hydrochloride have been known for some tune. For instance, U.S. Pat. No. 3,067,099 discloses a method of producing vancomycin through cultivation of a vancomycin-producing strain of *Streptomyces Orientalis* under aerobic conditions in a culture medium containing assimilable sources of carbohydrate, organic nitrogen and inorganic salts. Separation and purification processes for separating vancomycin hydrochloride from fermentation broth have also been disclosed in literature and patent documents. U.S. Pat. No. 4,440,753 describes an example of an isolation method and purification process for forming precipitate by isopropanol, ethanol or acetone. U.S. Pat. No. 4,868,285 discloses an example of an isolation method and filtration process to collect a compound of imidazole and vancomycin. However, in many of these processes, formed nantokite or imidazole compound may decompose and contaminate the final vancomycin product. Further, slurry may form when using isopropanol, ethanol or acetone to isolate vancomycin, which is hard to filter.

U.S. Pat. No. 5,853,720 discloses a process for purifying vancomycin hydrochloride that combines the preparative chromatography on a silica gel column containing an alkaline water-methanol mobile phase and the precipitation with ethanol from a salt-water-ethanol solution. The process produces vancomycin hydrochloride solid by lyophilization, spray drying or precipitation of pH 3, 100 g/L concentrate, which is obtained through a series of operations like microfiltration of vancomycin broth, then macro porous resin adsorption and elution, concentration and desalting, discoloring with activated carbon. The vancomycin solution is spray dried at an inlet temperature of 115-130° C. and an outlet temperature of 85±5° C. Usually, the content of water in vancomycin hydrochloride is about 4%, therefore it has been practice to additionally dry vancomycin hydrochloride in a rotation vacuum dryer at a temperature of 45-50° C. to obtain a dry solid product. This patent mentions that a chromatographic purity of vancomycin hydrochloride solution is about 93%. However, the patent does not appear to indicate the chromatographic purity and impurity levels of the final dry product. Experts and experienced technicians can appreciate that chromatographic purity of the obtained vancomycin hydrochloride product may decrease significantly after spray drying under high temperature conditions and vacuum drying at medium 'temperature conditions, resulting in increased impurity level and darker product color.

U.S. Pat. No. 7,018,804 discloses a method for preparing high purity vancomycin hydrochloride. In this patent, vancomycin hydrochloride concentrate with a HPLC purity of not less than 95% based on the EP method is obtained through a series of column purification processes, including strong acid type ion exchange resin chromatography, weak base type ion exchange resin column and aluminum oxide column chromatography, and hydrophobic resin chromatography. The final vancomycin hydrochloride product is obtained through precipitation by adding multiple (e.g., 5) times volumes of acetone and drying the resultant solution under vacuum conditions at a temperature of 40° C. It is note that this drying method would likely elevate the impurity level in the final product. Moreover, using the described method, residual solvents can't be removed completely to meet the corresponding requirements of, e.g., the International Conference on Harmonisation of Technical Requirements for Registration of Pharmaceuticals for Human Use (ICH).

M. Nieto and H. R. Perkins, in their publication, "Physicochemical Properties of Vancomycin and lodovancomycin and their Complexes with Diacetyl-L-lysyl-D-alanyl-D-alanine," Biochem. J. (1971) 123, 773-787, observed aggregation of vancomycin in an aqueous solution. The structure of aggregated glycopeptides remained uncharacterized. The publication described that aggregation is influenced by many factors such as ionization degree of phenol, hydrogen bond, etc.

Through addition of appropriate excipients such as surfactants or carbohydrates to reduce the forming of aggregates, the limiting concentration of vancomycin hydrochloride in water can be increased.

Due to thermal instability of vancomycin hydrochloride, the solution is typically prepared at a relative low temperature to avoid an increase in impurity level. Even if the solution is dried at a low temperature and under high vacuum conditions, the chromatographic purity of vancomycin hydrochloride will inevitably decrease. The lyophilization at low temperature will cause chromatographic purity to decrease by about 0.5% or more. For instance, the purity level of the solution will decrease by more than 1.0% through vacuum drying at 40° C. within 8 hours. The mainly-increased impurity is desamidovancomycin.

U.S. Pat. No. 6,001,800 discloses a method for preparing spray dried erythropoietin, and the dry erythropoietin powder produced thereby. The patent discloses that through addition of mannitol, glycine and sodium citrate as stabilizers and dispersants, active substances with appropriate ranges of particle size can be obtained.

U.S. Pat. No. 6,479,049 discloses a method and composition for the dry powder formulation of cytokines, especially interferons. The patent mentions interferon, to which carbohydrates, polypeptides and amino acids are added as a carrier. Appropriate excipients are added to improve product stability.

Excipients were reported to be used in vancomycin hydrochloride intravenous infusion in order to improve vancomycin stability and solubility such as Meek, a lyophilized generic product containing 100 mg each of D-mannitol and PEG 400 per 500 mg of vancomycin hydrochloride injection. Moreover, it was also reported that Meek was less nephrotoxic than a conventional preparation without addition of excipients, as noted by Naoko Hodoshima, Drug Metab. Pharmacokin. 19(1): 68-75 (2004).

U.S. Patent Application Publication No. US 2013/0009330 discloses a preparative method of a stable and easily-soluble powdered vancomycin formulation for injection through a spray drying process after dissolving a mixture of 10-20% by weight vancomycin HCl, about 2-4% by weight PEG, and 2-4% by weight mannitol. However, impurity B specified in European Pharmacopeia can't be significantly controlled by using this formulation. Moreover, the concentration of the vancomycin hydrochloride solution is limited at 10-20%, and it is not easy for further filling of spray dried powder due to low density.

Presently, drying methods used for drying vancomycin hydrochloride include lyophilization, vacuum drying and spray drying.

Lyophilization tends to be the main drying process for the production of both preparations and active substances. During lyophilization of active substances, it is difficult to ensure application of aseptic technology at each stage of the production process, including, e.g., during loading, unloading and powder collection processes, thereby making it very difficult to obtain sterile active substances. Therefore, it is frequently necessary to repeatedly dissolve non-sterile active substances and lyophilize the substances to get sterile powder for injection in vials. This inefficient production process results in large investments In specialized equipment, low production yields, poor efficiency and high operation costs, which may not be applicable for the production of large strengths above, e.g., 10 g/vial because of the high ratio of vials that tend to break during the process, as well as the undesirably long lyophilization cycle. The prolonged production cycle tends to affect product quality due to a higher impurity level.

If using vacuum drying, as a heat-sensitive substance, vancomycin should be dried at a low temperature and under high vacuum conditions. However, because vancomycin tends to combine with water and some polar solvent, it is hard to completely remove the water or the polar solvent. A significant problem in vacuum drying is that the residual solvent level can't meet the ICH's requirements. Moreover, prolonged drying time will result in a higher impurity level.

There has been discussion of using spray drying in industrial production of vancomycin hydrochloride under high temperature conditions. In spray drying, a vancomycin hydrochloride fluid solution is transformed into a dry-form product by spraying the solution into, e.g., a heat drying device. The resultant spray-dried product is typically in powder form. Spray drying, however, can result in degradation of vancomycin hydrochloride. During preparation of the vancomycin chloride solution, vancomycin chloride concentration levels can exceed 20%, thereby increasing the viscosity of the solution and forming an aggregate (e.g., semi-solid jelly) or precipitate that may block equipment, e.g., production filters. The implementation of 15% vancomycin hydrochloride concentration levels has been reported, such as, e.g., in US2013009330.

Solution stability should be considered since the concentrate maybe stored for more than twenty-four hours because additional preparation time may be required for each operation. There exists the unsolved problem in industrial production on how to ensure stability of vancomycin hydrochloride solution without increasing impurity and forming precipitate within, for example, forty-eight hours. Since the temperature during spray drying may exceed above 80° C., ensuring the stability of vancomycin hydrochloride may be a barrier to production.

A further problem with spray drying is that the spray dried vancomycin powder will be filled directly into, e.g., vials. Accordingly, the process should allow for reconstitution time at least as fast as the lyophilized formulations. Spray dried vancomycin tends to have smaller particle sizes and the reconstitution time tends to be longer than that of the loose-structured lyophilized product.

In order to reduce the possibility of side effects, a high chromatographic purity of antibiotics is very important in certain applications, which cannot be achieved by hitherto purification processes.

The present disclosure provides a novel system and a novel method for producing high purity and high potency vancomycin hydrochloride that solve the afore-discussed problems.

SUMMARY OF THE DISCLOSURE

According to one non-limiting example of the disclosure, a system and a method are provided for producing high purity and high potency vancomycin hydrochloride from a non-sterile or sterile vancomycin hydrochloride substance with a low impurity level. According to the present disclosure, a non-sterile or sterile vancomycin hydrochloride drug substance with low impurity level can be obtained through a fermentation process of *Amycolatopsis Orientalis* on appropriate media containing carbon, nitrogen and inorganic salts at appropriate cultivation conditions to obtain vancomycin broth, followed by a series of purification steps to obtain above 20% (w/w) vancomycin hydrochloride ultra-concentrate, as well as final evaporation at high temperature in a short time to remove solvents. This obtained sterile vancomycin hydrochloride drug substance can be directly subdivided to powder for injection in patients.

The present disclosure provides a method to prepare spray dried vancomycin hydrochloride powder. This method includes using vancomycin hydrochloride solution with a chromatographic purity of not less than 95%, adding stabilizer and solubilizer to improve solution stability, as well as to increase its concentration to 20-30%, and spray drying the solution to form spray dried vancomycin hydrochloride powder with a impurity B (specified in EP monograph) level of not more than 1.5%.

The disclosure provides many advantageous over existing systems and processes for making vancomycin hydrochloride. For instance, the disclosure resolves, among other things, the solution stability of vancomycin hydrochloride at high concentrations by increasing the concentration to 20-30%, which significantly improves efficiency of the spray drying process. The higher concentration levels also improve quality, dissolving characteristics, bulk density of the obtained drug substance powder, impurity level control, yield to realize large scale production, while reducing time and cost requirements of production operations.

According to an aspect of the disclosure, a method is provided for preparing spray dried powder containing vancomycin hydrochloride. The method comprises: providing a vancomycin hydrochloride solution with a chromatographic purity of at least 95%; adding an excipient to the vancomycin hydrochloride solution to form a mixture solution of the vancomycin hydrochloride solution and the excipient; concentrating the mixed solution of the vancomycin hydrochloride solution and the excipient to form a 20% to 30% vancomycin concentrate; filtering the vancomycin concentrate to form a final filtrate; and spray drying the final filtrate to form a spray dried vancomycin hydrochloride powder with EP impurity B level of not more than 1.5%.

The method may further comprise transferring the spray dried vancomycin hydrochloride powder with EP impurity B level of not more than 1.5% into a gamma irradiated single use bag.

The excipient may comprise at least one of: a stabilizer; a solubilizer; a saccharide; a polyol; polyethylene glycol-400 (PEG-400); and a surfactant.

The method of providing the vancomycin hydrochloride solution with the chromatographic purity of at least 95% may comprise dissolving a vancomycin hydrochloride active pharmaceutical ingredient (API) in purified water.

The mixture solution of the vancomycin hydrochloride solution and the excipient may comprise: about 5-35% by weight of saccharide; about 10-50% by weight of polyols; about 10-50% by weight of PEG-400; and about 0.005-0.05% by weight of surfactants.

The excipient may comprise a surfactant. The saccharide may include fructose, trehalose, sorbose, lactose and glucose. The polyol may include mannitol. The surfactant may include polyoxyethylene sorbitan monooleate (tween 80), poloxamer 188, polyethylene glycol (35), castor oil hydrogenated (RH-35), polyethylene glycol (40), castor oil hydrogenated (RH-40), and polyglycol 12 hydroxystearate.

The mixture solution of the vancomycin hydrochloride solution and the excipient may comprise: about 25% by weight trehalose; and about 0.01% by weight of polyoxyethylene sorbitan monooleate (tween 80).

The method of filtering the vancomycin concentrate to form the final filtrate may comprise: passing the vancomycin concentrate through at least one of a reverse osmosis membrane and a 200-800 Da nano-filtration membrane; and controlling a temperature during filtering so that it does not exceed 20° C.

The vancomycin concentrate may have a pH of about 2.0-4.0 and may be stored at a temperature of about 2-8° C. for not more than about 120 hours.

The method of spray drying may comprise: turning on a spray dryer, including a heating device; controlling an inlet temperature and an outlet temperature; turning on a feeding switch; maintaining the spray dryer in a positive pressure; and using above 95% nitrogen as a heating gas, wherein the inlet temperature is controlled to about 160° C. to about 240° C. and the outlet temperature is controlled to about 80° C. to about 120° C.

The spray dried vancomycin hydrochloride powder may be sterile.

The method may further comprise: filling the spray dried vancomycin hydrochloride powder in a dosage form; and sealing the dosage while vacuuminzing and injecting nitrogen gas into the vial to provide a sealed dosage form.

The sealed dosage form may comprise a dosage strength of about 0.5 g, about 0.75 g, about 1.0 g, about 2 g, about 5 g, about 10 g or about 20 g.

The sterile vancomycin hydrochloride powder may be administrable orally or injectable intravenously.

The spray dried vancomycin hydrochloride powder may have water content below 3%.

The dosage form may comprise a vial or a capsule.

According to a further aspect of the disclosure, a method is provided for preparing spray dried powder containing vancomycin hydrochloride that comprises: providing a vancomycin hydrochloride solution with a chromatographic purity of at least 95%; adding a stabilizer and a solubilizer to the vancomycin hydrochloride solution to form a mixture solution of the vancomycin hydrochloride solution, the stabilizer and the solubilizer; concentrating the mixture solution to form a 20% to 30% vancomycin concentrate; and spray drying the vancomycin concentrate to form a spray dried vancomycin hydrochloride powder with EP impurity B level of not more than 1.5%.

The method may further comprise filtering the vancomycin concentrate to form a final filtrate.

According to a still further aspect of the disclosure, a system is provided for preparing spray dried powder containing vancomycin hydrochloride. The system comprises: a tank that receives a vancomycin hydrochloride solution with a chromatographic purity of at least 95%; a mixer that mixes the vancomycin hydrochloride solution and an excipient that is added to produce a mixture solution of the vancomycin hydrochloride and the excipient; a membrane that concentrates the mixture solution to produce a 20% to 30% vancomycin concentrate; a filter that filters the vancomycin concentrate to form a final filtrate; and a spray dryer that dries the final filtrate to form a spray dried vancomycin hydrochloride powder with EP impurity B level of not more than 1.5%.

Additional features, advantages, and embodiments of the disclosure may be set forth or apparent from consideration of the detailed description and drawings. Moreover, it is to be understood that the foregoing summary of the disclosure and the following detailed description and drawings are exemplary and intended to provide further explanation without limiting the scope of the disclosure as claimed.

BRIEF DESCRIPTION OF THE DRAWINGS

The accompanying drawings, which are included to provide a further understanding of the disclosure, are incorporated in and constitute a part of this specification, illustrate embodiments of the disclosure and together with the detailed description serve to explain the principles of the disclosure. No attempt is made to show structural details of the disclosure in more detail than may be necessary for a fundamental understanding of the disclosure and the various ways in which it may be practiced. In the drawings.

Figure 1:
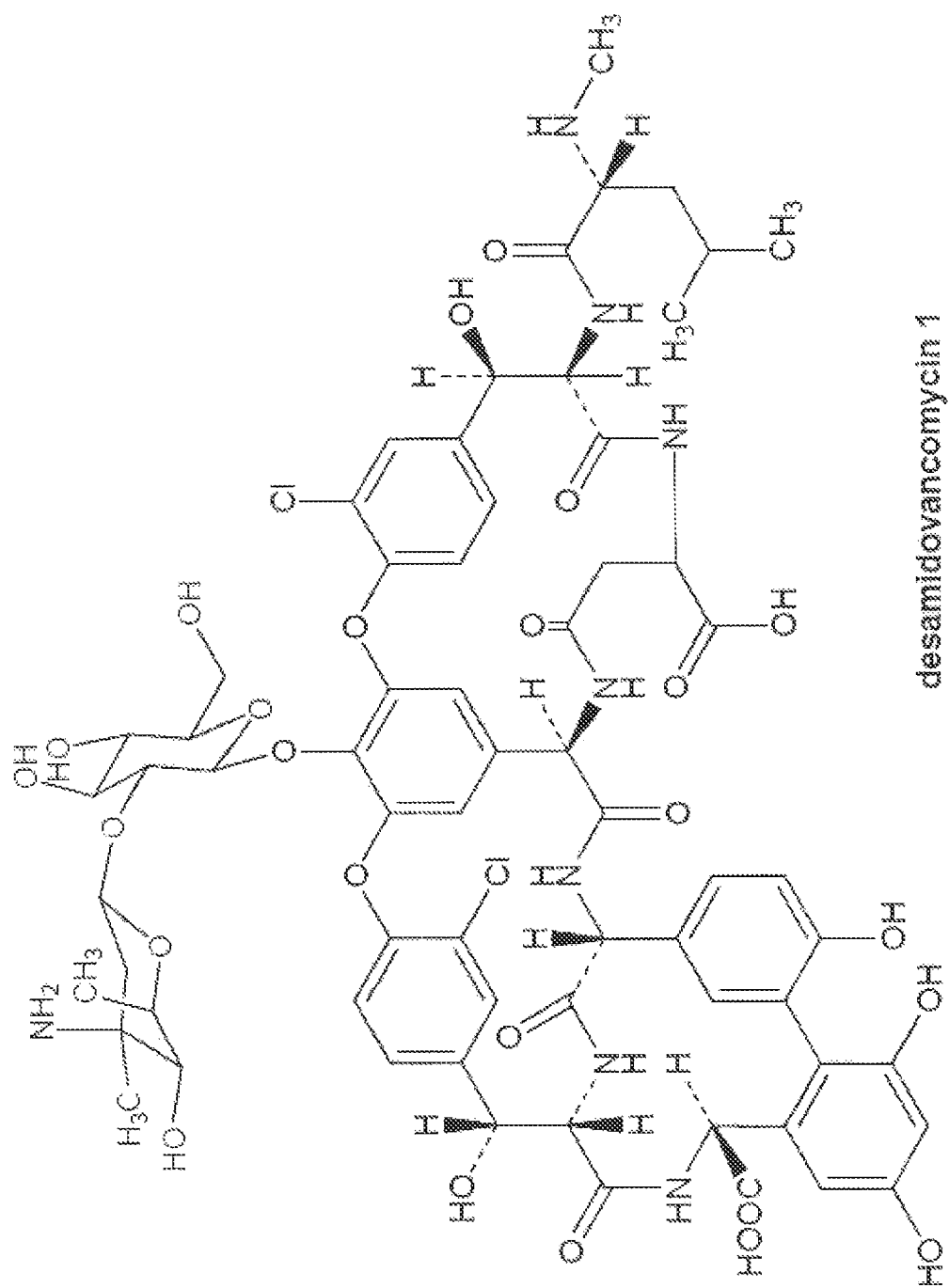
FIG. 1 shows a first isomeric form of desamidovancomycin.
Figure 2:
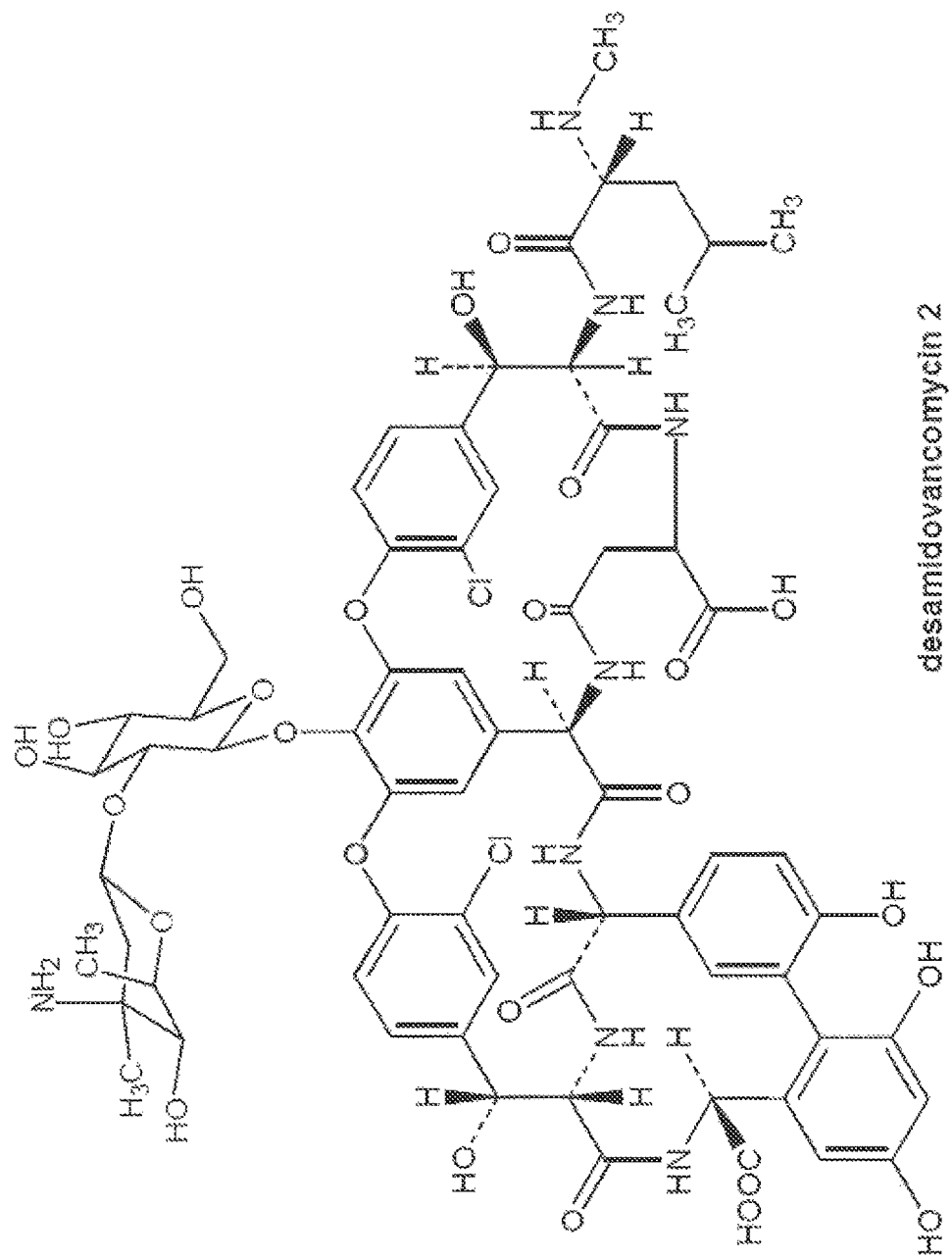
FIG. 2 shows a second isomeric form of desamidovancomycin.
Figure 3:
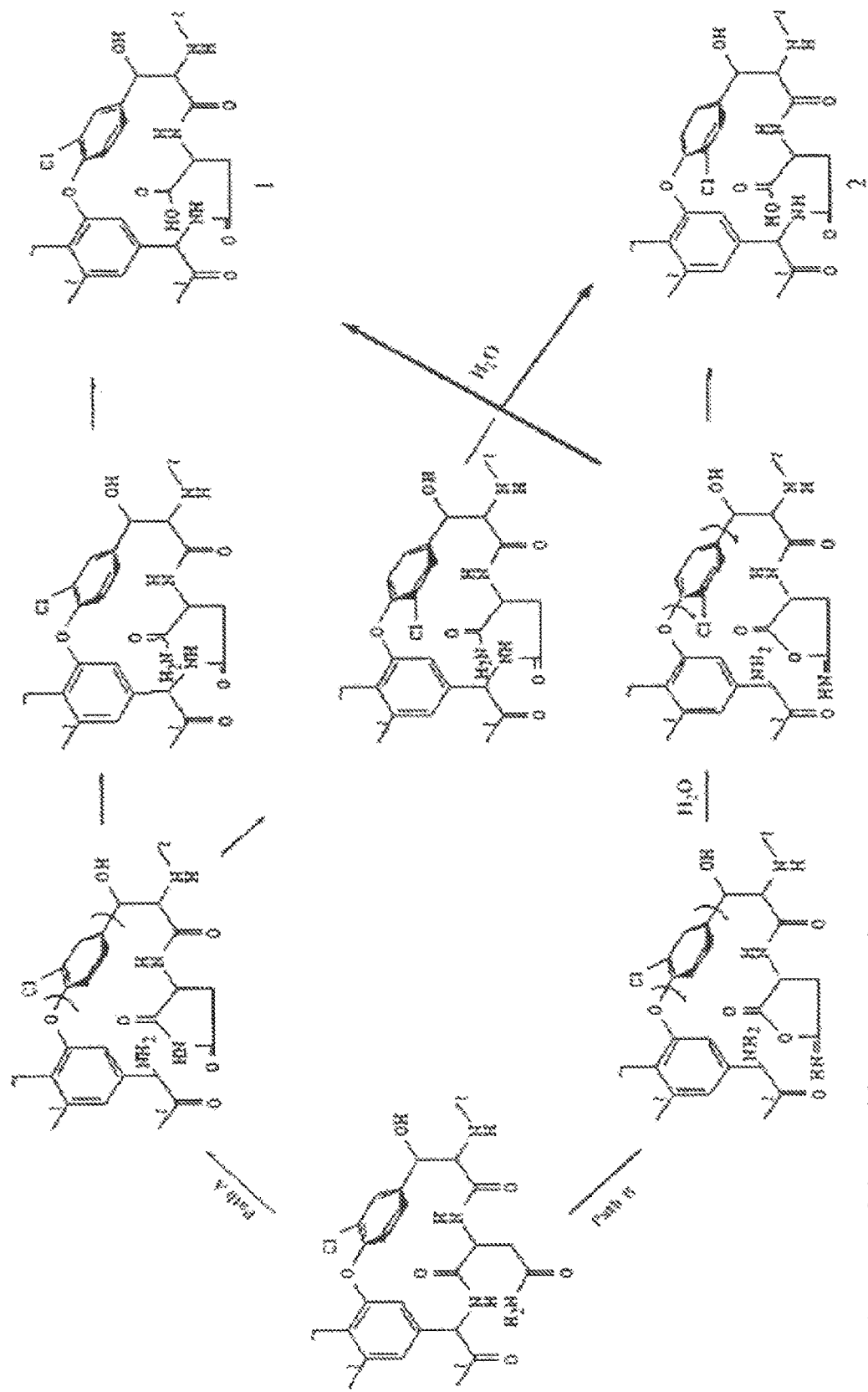
FIG. 3 shows two pathways for conversion from vancomycin to succinimide, and for conversion from succinimide to desamidovancomycin.

The present disclosure is further described in the detailed description that follows.

DETAILED DESCRIPTION OF THE DISCLOSURE

The disclosure and the various features and advantageous details thereof are explained more fully with reference to the non-limiting embodiments and examples that are described and/or illustrated in the accompanying drawings and detailed in the following description. It should be noted that the features illustrated in the drawings are not necessarily drawn to scale, arid features of one embodiment may be employed with other embodiments as the skilled artisan would recognize, even if not explicitly stated herein. Descriptions of well-known components and processing techniques may be omitted so as to not unnecessarily obscure the embodiments of the disclosure. The examples used herein are intended merely to facilitate an understanding of ways in which the disclosure may be practiced and to further enable those of skill in the art to practice the embodiments of the disclosure. Accordingly, the examples and embodiments herein should not be construed as limiting the scope of the disclosure. Moreover, it is noted that like reference numerals represent similar parts throughout the several views of the drawings.

According to an aspect of the disclosure, a highly-efficient industrial system and method are provided herein for producing high potency and high purity vancomycin hydrochloride. The method includes the addition of excipients at an optimal point in the preparation process to a vancomycin hydrochloride solution. Excipients used in the method may include stabilizers and/or solubilizers. For instance, the excipients may include carbohydrates, polyols, amino acids, organic amines, salts, polymers and surfactants, of which carbohydrates and polyols may be used as non-specific stabilizers. When using carbohydrates as stabilizers, it may be desirable to avoid reducing carbohydrates. Sucrose and trehalose are good choices. Mannitol may be used as a stabilizer and a solubilizer. Trehalose is a stable reducing sugar composed of two glucose molecules constructed by a,a,1,1-glucosidic bond that may provide good protection for organisms because trehalose will form a protection membrane on the cell surface at heavy conditions such as higher or lower temperature, high osmotic pressure and dryness to protect protein molecules from denaturation and deactivation to maintain the life cycle and bio-characteristics of organisms. Many of the species showing extraordinary resistance to adverse external conditions contain a lot of trehalose in their organisms. However, this similar effect has not been observed for the other natural carbohydrates, such as, e.g., sucrose and glucose. This distinct characteristic of trehalose makes it a good activity-protective agent of protein pharmaceuticals, enzymes, vaccines and other biological products.

Amino acids can be used to improve the stability of preparations, especially for some protein preparations. The combination of histidine, glycine, sodium aspartate, glutamine, lysine hydrochloride and 5% mannitol in 10 mM phosphate buffer (pH7.0) can be used to inhibit the aggregate forming of keratinocyte growth factor (KGF).

According to an aspect of the disclosure, excipients are added in the spray drying process to improve stability and to improve product quality, even under severe drying conditions.

Further, an appropriate solubilizer should be added to the vancomycin hydrochloride in the spray drying process, since spray dried vancomycin tends to have smaller particle sizes and the reconstitution time tends to be longer than that of the loose-structured lyophilized product.

Active substances may be fixed on an amorphous matrix, which has a high viscosity environment, to ensure low molecular mobility and reaction activity. Therefore, the chosen excipient should perform well in embedding or facilitating the embedment of the active substance in the amorphous matrix, as well as improving its glass temperature. Compatibility of active substances, effects on particle forming, and dispersity and flowability should be considered, as will be understood and appreciated by those having ordinary skill in the art.

Figure 4:
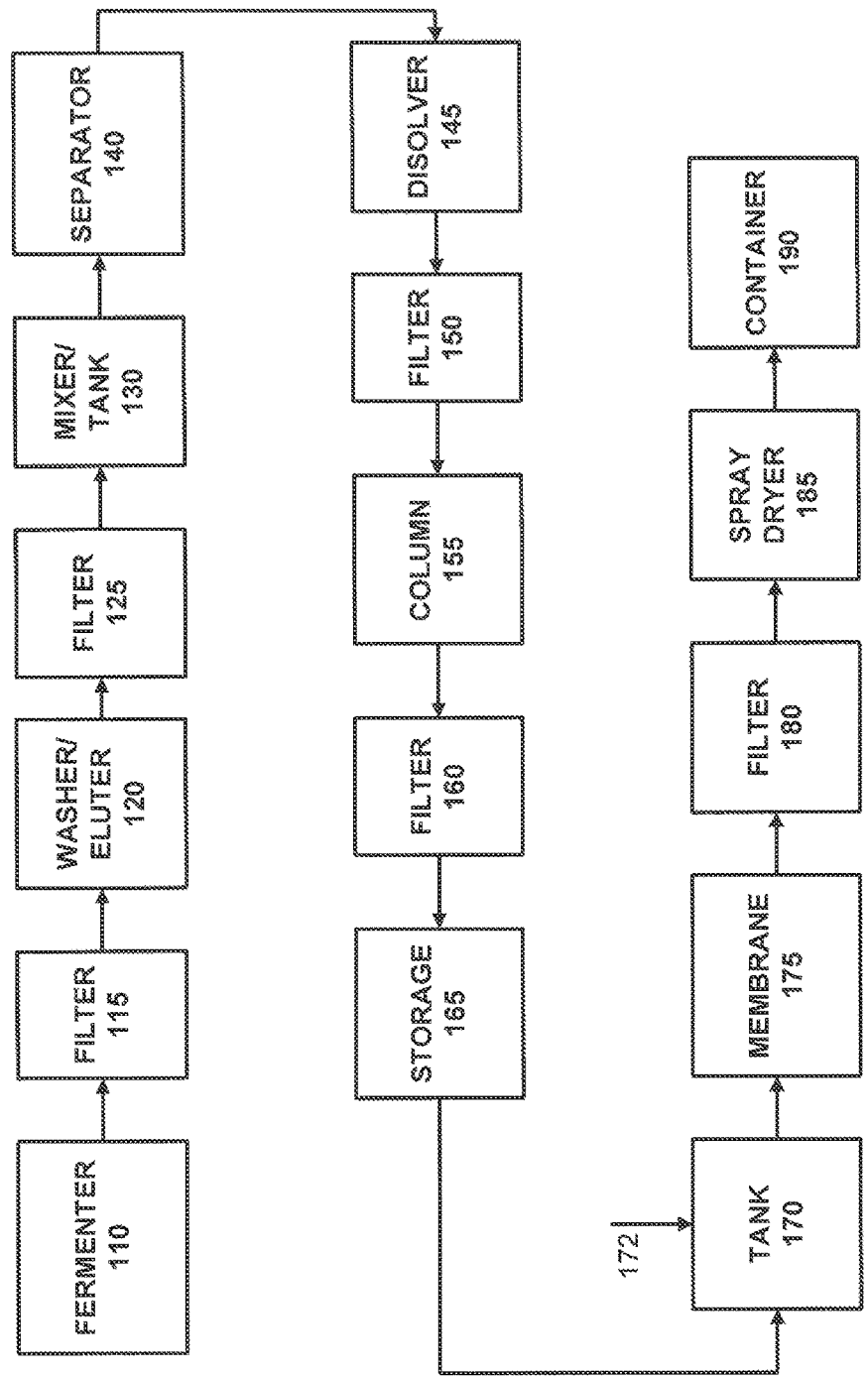
FIG. 4 shows an example of a system for producing high purity and high potency vancomycin hydrochloride, according to the principles of the disclosure.

FIG. 4 shows an example of a system 100 for producing high potency and high purity vancomycin hydrochloride powder that may be filled directly into, e.g., a vial. The system 100 includes a tank 170, a membrane 175, a filter 180, and a spray dryer 185. The system 100 may comprise a container 190. The system 100 may comprise a fermenter 110, a filter 115, a washer/eluter 120, a filter 125, a mixer/tank 130, a separator 140, a dissolver 145, a filter 150, a column 155, a filter 160, and/or a storage 165.

According to an aspect of the disclosure, the high purity sterile vancomycin hydrochloride powder produced by the system 100 may be transferred into, e.g., single use bags (not shown). The single use bags may be sterilized using gamma irradiation, or other mechanism that sufficiently sterilizes the bags.

Alternatively, the high purity sterile vancomycin hydrochloride powder produced by the system 100 may be transferred into an immediate bulk container via an isolator, as is known in the art.

In the fermenter 110, a fermentation process of *Amycolatopsis Orientalis* is carried out on an appropriate media containing carbon, nitrogen and inorganic salts at appropriate cultivation conditions. The fermenter 110 may produce a vancomycin broth, which may undergo a series of purification operations to get a concentrate with a chromatographic purity of vancomycin above 95%. By adding excipients, the concentration of vancomycin hydrochloride can be increased to 20-30%. Then, the resultant solution may be spray dried to get a sterile (or non-sterile) vancomycin hydrochloride drug substance, which may be filled under aseptic conditions to get preparations.

Referring to FIG. 4, *Amycolatopsis Orientalis*, SIP143491, may be introduced into the fermenter 110, e.g., as described in Chinese Patent Application No. CN01132048.6. The cultivation may start from inoculum preparation, then 1st stage seeding and 2nd stage seeding expansion until fermentation at a temperature of about 24-34° C. and a pressure of about 0.01-0.08 Mpa for 4-6 days to get a vancomycin broth. Oxygen dissolving and pH may be controlled during fermentation. The pH of the vancomycin broth may be adjusted to about 8.5-10.5 with, e.g., sodium hydroxide solution, as described in Patent 200710198599.4. The vancomycin broth may be delivered to, and passed through the filter 115 to get a clear filtrate.

The filter 115 may include, e.g., a 0.02-0.5 μm ceramic membrane, as described in Patent 200710198599.4 to filter the vancomycin broth into a clear filtrate. The clear filtrate is forwarded to the washer/eluter 120.

The washer/eluter 120 may include, e.g., a macroporous resin. The clear filtrate from the filter 115 is passed through the macroporous resin and the vancomycin may be eluted down with an acid solution containing solvent after water washing. The eluent include, e.g., a hydrochloric acid solution containing ethanol. An appropriate amount of activated carbon may be added into the collected elate for discoloring before forwarding the eluate to the filter 125 to obtain vancomycin solution with a concentration of about 1.00 mg/mL.

After concentration at the filter 125, the concentrate may be precipitated and about 6% to about 10% (W/V) of $NH_4HCO_3$ may be added to the vancomycin solution in the mixer/tank 130. The pH of the vancomycin solution may be adjusted to about 7.5-8.5 with a base, such as, e.g., ammonia. The solution may be stirred for about 45-60 minutes while the vancomycin precipitates from the solution. The precipitation temperature should be controlled to about 10-20° C. The solution may be kept still for about 16±2 hours and then separated to obtain solid vancomycin base from the solution.

The vancomycin solution may be provided to the separator 140 to separate the vancomycin base from the solution. The vancomycin base may be washed with ethanol to replace the residual solution and get vancomycin crude. The chromatographic purity of the resultant vancomycin base is not less than 80% (HPLC).

The vancomycin crude may be dissolved with purified water in a dissolver 145, e.g., as described in Patent 200710187300.5, to get a vancomycin solution. The dissolved vancomycin solution may be passed through a filter 150 to obtain a clear filtrate. The filter 150 may include, e.g., a 0.01-0.5 μm ceramic membrane.

The filtrate from the filter 150 may be delivered to and passed through an ion-exchange resin column 155 to get a qualified eluate with about 95% vancomycin B. The ion-exchange resin in the column 155 may include, e.g., a cation ion exchange sephadex gel (Sephadex), a sepharose gel (Sepharose), or the like. Vancomycin filtrate is loaded in the column 155 in acid condition, while it is eluted down in base condition by adding, e.g., a basic metal salt, an ammonium salt, or the like. Normally, $NH_4+$ and $Na+$ salts are used such as NaCl, $NH_4HCO_3$, $(NH_4)_2CO_3$, and the like.

Eluate fractions with above 93% vancomycin B are collected for combining to obtain the mixed qualified eluate with about 95% vancomycin B (according to HPLC method in USP monograph). Then, the qualified eluate is forwarded to the filter 160 where it may undergo ultra-filtration and nano-filtration to get 12-18% (or higher) vancomycin hydrochloride concentrate (a vancomycin solution with a chromatographic purity of not less than 95%). The filtered concentrate may be placed into to storage (e.g., a container, a tank, or the like) and stored at 2-8° C. for a predetermined time (e.g., 48 hours, 72 hours, or the like), but less than, e.g., 120 hours.

Figure 5:
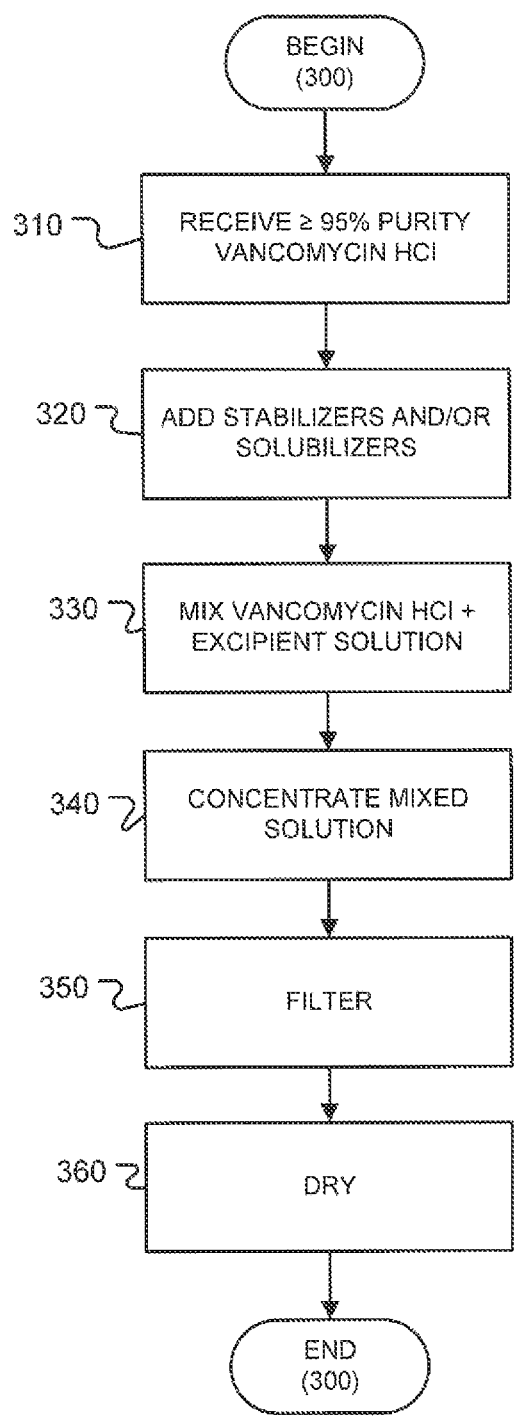
FIG. 5 shows an example of a process for producing high purity and high potency vancomycin hydrochloride, according to the principles of the disclosure.

FIG. 5 shows an example of a process 300 for producing high purity and high potency vancomycin hydrochloride, according to the principles of the disclosure.

Referring to FIGS. 4 and 5, the vancomycin hydrochloride concentrate with a chromatographic purity of not less than 95% is received in the tank 170 (Step 310). The concentrate may be received from the storage 165, or directly from the filter 160. Stabilizers and/or solubilizers 172 are added to the vancomycin hydrochloride solution to get a mixture solution of vancomycin hydrochloride and excipients (Step 320). The mixture solution may be stirred in the tank 170 by a mixer (not shown) (Step 330). The stabilizers may comprise saccharides and/or polyols. The solubilizers may comprise polyethylene glycol-400 (PEG-400) and/or surfactants. The amount of saccharides added to the mixture solution may be, e.g., about 5-35% by weight of dry vancomycin hydrochloride. The concentration of polyols may be, e.g., about 10-50% by weight of dry vancomycin hydrochloride. The concentration of PEG-400 may be, e.g., about 10-50% by weight of dry vancomycin hydrochloride. The amount of surfactants may be, e.g., about 0.005-0.05% by weight of dry vancomycin hydrochloride.

The saccharide may include, e.g., fructose, trehalose, sorbose, lactose, glucose, or the like. The polyol may include, e.g., mannitol, or the like. The surfactant may include, e.g., polyoxyethylene sorbitan monooleate (tween 80), poloxamer 188, polyethylene glycol (35), castor oil hydrogenated (RH-35), polyethylene glycol (40), castor oil hydrogenated (RH-40), polyglycol 12 hydroxystearate, or the like.

The amount of trehalose added in the mixture solution may be, e.g., about 25% by weight, of dry vancomycin hydrochloride.

The amount of polyoxyethylene sorbitan monooleate (tween 80) added to the mixture solution may be, e.g., about 0.01% by weight of dry vancomycin hydrochloride.

The mixture solution may be concentrated in the membrane equipment 175 to obtain 20-30% vancomycin concentrate (Step 340). The membrane equipment 175 may include, e.g., a reverse osmosis membrane. The temperature during concentration (e.g., in the membrane equipment 175)

may be controlled so as not to exceed 20° C. The vancomycin concentrate may be delivered to the filter 180 for filtration.

The filter 180 receives and filters the vancomycin concentration, outputting a final filtrate (Step 350). The filter 180 may include, e.g., a 200-800 Da nano-filtration member. The temperature during filtration may be controlled so as not to exceed 20° C. The final filtrate may be delivered to a spray dryer 185 to get spray dried vancomycin hydrochloride powder with EP impurity B level of not more than 1.5% (Step 360). The pH of the spray dried vancomycin hydrochloride powder may be, e.g., about 2.0-40. The spray dried vancomycin hydrochloride powder may have water content that is below 3%.

The spray dryer 185 may comprise an atomizer (not shown), a feedstock pump (not shown), a gas heater (not shown), a gas disperser (not shown), and a drying chamber (not shown). The spray dryer 185 may further comprise a system for cleaning exhaust gases (not shown) and a system for recovering vancomycin hydrochloride powder (not shown) and for injecting the powder into, e.g., vials. The spray dryer 185 may further comprise a cyclone. The spray dryer 185 may comprise, e.g., a Buchi B-290 spray dryer, a nano spray dryer, or the like.

According to an aspect of the disclosure, the spray dryer 185 may be operated by a method that comprises: (1) turning on the spray dryer 185, including the heating device (not shown); (2) controlling and maintaining inlet temperature to, e.g., about 160-240° C., and controlling and maintaining outlet temperature to, e.g., 80-120° C.; (3) turning on the feeding switch (not shown); (4) maintaining the spray dryer 185 at positive pressure; and (5) using above 95% nitrogen as heating gas.

The vancomycin hydrochloride powder delivered from the spray dryer 185 may be sterile or non-sterile. If the spray dried vancomycin hydrochloride powder is sterile, then it may be filled into vials with Auger, e.g., using an aseptic tilling machine (not shown), and then capped while vacuuminzing and filling nitrogen. The dosage strength may include, e.g., about 0.5 g, 0.75 g, 1.0 g, 2 g, 5 g, 10 g, or 20 g.

Further, sterile vancomycin hydrochloride powder may be administered by oral or injectable form.

Preferably, the vancomycin hydrochloride solution with a chromatographic purity of not less than 95% is prepared by dissolving vancomycin hydrochloride active pharmaceutical ingredient (API) in purified water, or in water for injection.

Preferably, the amount of saccharides is 5-35% by weight of dry vancomycin hydrochloride, the concentration of polyols is 10-50 wt. % and the concentration of PEG-400 is 10-50 wt. %, the amount of surfactants is 0.005-0.05% by weight of dry vancomycin hydrochloride.

Preferably, the saccharide includes trehalose, fructose, sorbose, lactose and glucose, the polyol includes mannitol, the surfactant includes polyoxyethylene sorbitan monooleate (tween 80), poloxamer 188, polyethylene glycol (35), castor oil hydrogenated (RH-35), polyethylene glycol (40), castor oil hydrogenated (RH-40), and polyglycol 12 hydroxystearate.

Preferably, the amount of trehalose is 25% by weight of dry vancomycin hydrochloride, and the amount of polyoxyethylene sorbitan monooleate (tween 80) is 0.01% by weight of dry vancomycin hydrochloride.

Preferably, the membrane concentration equipment 175 (shown in FIG. 4) includes a reverse osmosis membrane and a 200-400 Da nano-filtration membrane. The temperature during concentration is controlled not more than 20° C.

Preferably, the pH of the final concentrate is 2.0-4.0, and the concentrate is stored at 2-8° C. for not more than 120 hours.

Preferably, for the spray drying operation (Step 360), the operation includes turning on the spray dryer 170 and heating device (not shown, in spray dryer 170, FIG. 4), controlling inlet temperature and outlet temperature at 160-240° C. and 80-120° C., respectively, turning on feeding switch (not shown, in spray dryer 170), keeping the system in positive pressure and using above 95% nitrogen as heating gas.

Preferably, the spray dried vancomycin hydrochloride powder can be sterile or non-sterile.

Preferably, if the spray dried vancomycin hydrochloride powder is sterile, it can be filled in vials using, e.g., an aseptic filling machine with Auger, and then capped while vacuuminzing and filling nitrogen. The strengths are 0.5 g, 0.75 g, 1.0 g, 2 g, 5 g, 10 g and 20 g.

Preferably, the sterile vancomycin hydrochloride can be administered by oral or injectable form.

Preferably, the spray dried vancomycin hydrochloride powder has water content below 3%.

In the system 100 and/or process 300, by adding an appropriate ratio of excipients to a vancomycin solution at the optimal point in the process, as disclosed herein, the vancomycin hydrochloride solution is stabilized and the concentration of vancomycin is increased to 20-30%, while simultaneously increasing drying efficiency. Further, the instant disclosure can be implemented to provide high concentration, sterile vancomycin hydrochloride drug substances with favorable bulk density, which allow for easy filling of vials. The optimally added excipients improve product stability in spray drying processes; reduce the number of process steps; control and maintain low impurity levels; and improve product solubility and quality.

The present disclosure realizes commercial production of high quality and high potency vancomycin hydrochloride from fermentation to preparation and filling of sterile drug substances, then to sterile powder for injection after filling. Compared to existing technology, the production process disclosed herein shortens production time, has fewer production steps, reduces cost, and improves yield, allowing for implementation in industrial scale production.

The following examples are presented to illustrate the present disclosure. The disclosure is not to be considered limited by these examples nor the parameter ranges in these examples.

EXAMPLES

Example 1

Stability Study of Vancomycin Concentrates with Different Excipients

To 900 ml. of 25% vancomycin concentrate (batch No: 310121109; vancomycin B: 96.50%; 225 g of vancomycin in total), subdivided in nonuplicate, 100 ml each. To eight of them, added 5 g of trehalose, 5 g of mannitol, 5 g of glucose, 5 g of fructose, 5 g of glycine, 5 g of glutamine, 5 g of sorbose and 5 g of lactose, respectively, passed these eight solutions as well as the one without excipients through 0.22 μm filter, respectively, and stored the obtained filtrate at 2-8° C. in refrigerator. Observed clarity of the filtrate every 24 hours and the results are shown in Table I.

TABLE 1

Clarity of vancomycin concentrate at 2-8° C.
with different amounts of trehalose

| Amount of excipient (g) | Solution appearance after 24 hours | Solution appearance after 48 hours | Solution appearance after 72 hours | Solution appearance after 96 hours |
|---|---|---|---|---|
| 0 | White particle precipitate | White particle precipitate | White particle precipitate | Colloidal, without fluidity |
| 5 g trehalose | Clear | Clear | Clear | Clear |
| 5 g mannitol | Clear | Clear | Clear | Filamentous precipitate |
| 5 g glucose | Clear | Clear | White particle precipitate | White particle precipitate |
| 5 g fructose | Clear | Clear | White particle precipitate | White particle precipitate |
| 5 g glycine | Clear | White particle precipitate | White particle precipitate | White particle precipitate |
| 5 g glutamine | Clear | White particle precipitate | White particle precipitate | Colloidal, without fluidity |
| 5 g sorbose | Clear | Clear | White particle precipitate | White particle precipitate |
| 5 g lactose | Clear | Clear | White particle precipitate | White particle precipitate |

Based on the data in Table 1, it can be seen that appropriate excipients can improve the stability of vancomycin concentrate at 2-8° C., of which trehalose is the best one.

Example 2

Effect of Different Trehalose Concentration on Stability of Vancomycin Concentrate To 800 mL of 25% vancomycin concentrate (batch No: 310121109; vancomycin B: 96.50%; 200 g of vancomycin in total), subdivided in octuplicate, 100 mL (about 25 g of vancomycin) each.

To the eight portions, add 0 g, 1.25 g (5% of weight of vancomycin), 2.5 g (10% of weight of vancomycin), 3.75 g (15% of weight of vancomycin), 5 g (20% of weight of vancomycin), 6.25 g (25% of weight of vancomycin), 7.5 g (30% of weight of vancomycin) and 8.75 g (35% of weight of vancomycin) of trehalose, respectively, dissolved completely and filtered through 0.22 μm to get Filtrate A, B, C, D, E, F, CI and H, respectively. Stored all the obtained filtrates at 2-8° C. in a refrigerator, and observed clarity of the filtrates every 24 hours. The results are presented in Table. 2.

TABLE 2

Clarity of vancomycin concentrate at 2-8° C.
with different amount of trehalose

| Amount of trehalose | Solution appearance after 24 hours | Solution appearance after 48 hours | Solution appearance after 72 hours | Solution appearance after 96 hours | Solution appearance after 120 hours | Solution appearance after 144 hours |
|---|---|---|---|---|---|---|
| 0 | White particle precipitate | White particle precipitate | White particle precipitate | Colloidal, without fluidity | Colloidal, without fluidity | Colloidal, without fluidity |
| 5% | Clear | Clear | Clear | Clear | Filamentous precipitate | Filamentous precipitate |
| 10% | Clear | Clear | Clear | Clear | Clear | Filamentous precipitate |
| 15% | Clear | Clear | Clear | Clear | Clear | Clear |
| 20% | Clear | Clear | Clear | Clear | Clear | Clear |
| 25% | Clear | Clear | Clear | Clear | Clear | Clear |
| 30% | Clear | Clear | Clear | Clear | Clear | Clear |
| 35% | Clear | Clear | Clear | Clear | Clear | Clear |

Based on the data in Table 2, it can be seen that vancomycin concentrate is still clear after storage at 2-8° C. for 144 hours when the amount of added trehalose is 15%-35% by weight of vancomycin.

Example 3

Process Parameters Study on Spray Drying of Vancomycin Concentrate

Spray dryer: Buchi B-290.

Materials: vancomycin concentrate, batch No: 310121109; vancomycin B: 96.50%; Concentration: 20%.

Experiment process: in these embodiments, the spray drying was performed at three inlet temperatures of 170° C., 190° C. and 210° C., and for each inlet temperature, three outlet temperature ranges of 90-100° C., 100-110° C. and 110-120° C. were adopted, respectively.

For each embodiment, at the chosen inlet air temperature and the corresponding outlet air temperature by adjusting speed of feedstock pump, performed spray drying of 200 mL vancomycin concentrate, collected dry vancomycin powder and tested moisture, pH of 5% vancomycin solution, HPLC as well as OD of 10% vancomycin solution.

The batch numbers of spray dried vancomycin hydrochloride powder together with the corresponding inlet temperature and outlet temperature are listed as follows:

| Inlet temperature (° C.) | Outlet temperature (° C.) | Batch No of spray dried powder |
|---|---|---|
| 170° C. | 90-100° C. | 112001 |
|  | 100-110° C. | 112002 |
|  | 110-120° C. | 112003 |
| 190° C. | 90-100° C. | 112004 |
|  | 100-110° C. | 112101 |
|  | 110-120° C. | 112102 |
| 210° C. | 90-100° C. | 112103 |
|  | 100-110° C. | 112104 |
|  | 110-120° C. | 112105. |

The experimental records and results are described as follows:

TABLE 3-1

Records of spray drying

| | Test No. | | | |
|---|---|---|---|---|
| | 112001 | 112002 | 112003 | 112004 |
| Duration | 10:45-11:10 | 14:10-14:50 | 15:25-16:10 | 16:30-16:55 |
| Inlet Temperature (° C.) | 170 | 170 | 170 | 190 |
| Outlet Temperature (° C.) | 90-100 | 100-110 | 110-120 | 90-100 |
| Air volume (%) | 100 | 100 | 100 | 100 |
| Speed of pump (%) | 30 | 25 | 20 | 40 |
| Flow rate of nitrogen (mm) | 40 | 50 | 50 | 50 |
| System pressure (mbar) | 15 | 15 | 15 | 15 |

TABLE 3-2

Records of spray drying

| | Test No. | | | | |
|---|---|---|---|---|---|
| | 112101 | 112102 | 112103 | 112104 | 112105 |
| Duration | 8:35-9:05 | 10:02-10:35 | 11:05-11:40 | 15:00-15:30 | 16:10-16:55 |
| Inlet Temperature (° C.) | 190 | 190 | 210 | 210 | 210 |
| Outlet Temperature (° C.) | 100-110 | 110-120 | 90-100 | 100-110 | 110-120 |
| Air volume (%) | 100 | 100 | 100 | 100 | 100 |
| Speed of pump (%) | 30 | 25 | 50 | 40 | 30 |
| Flow rate of nitrogen (mm) | 40 | 50 | 50 | 40 | 50 |
| System pressure (mbar) | 15 | 15 | 15 | 15 | 15 |

TABLE 4-1

Test results of spray dried powder

| | Test No. | | | | |
|---|---|---|---|---|---|
| | Original test | 112001 | 112002 | 112003 | 112004 |
| Water (%) | NA | 6.2 | 5.9 | 6.7 | 5.9 |
| pH, 5% Conc. | 2.93 | 3.08 | 3.08 | 3.10 | 3.07 |
| $A_{450}$, 10% Conc. | 0.054 | 0:068 | 0.064 | 0.074 | 0.069 |
| Assay of vancomycin B (%) | 96.5 | 95.44 | 95.22 | 95.49 | 95.47 |
| Impurity $B_1$ | 0.79 | 0.89 | 0.90 | 0.89 | 0.88 |
| Impurity $B_2$ | / | 0.14 | 0.18 | 0.14 | 0.14 |
| Impurity $B_1$ and $B_2$ | 0.79 | 1.03 | 1.08 | 1.03 | 1.02 |

TABLE 4-2

Test results of spray dried powder

| | Test No. | | | | |
|---|---|---|---|---|---|
| | 112101 | 112102 | 112103 | 112104 | 112105 |
| Water (%) | 5.8 | 6.2 | 5.7 | 6.1 | 5.5 |
| pH, 5% Conc. | 3.05 | 3.08 | 3.01 | 3.02 | 3.05 |
| $A_{450}$, 10% Conc. | 0.067 | 0.067 | 0.062 | 0.062 | 0.075 |
| Assay of vancomycin B (%) | 95.34 | 95.24 | 95.13 | 95.14 | 95.02 |
| Impurity $B_1$ | 0.94 | 0.94 | 0.98 | 0.95 | 0.96 |
| Impurity $B_2$ | 0.19 | 0.18 | 0.19 | 0.16 | 0.25 |
| Impurity $B_1$ and $B_2$ | 1.13 | 1.12 | 1.17 | 1.11 | 1.21 |

Referring to the data in Tables 4-1 and 4-2, it can be seen that: (1) without addition of excipient, vancomycin B in the final dried powder decreased, at the same time, impurity $B_1$ and impurity $B_2$ increased; (2) the dried powders obtained at inlet air temperature of 170° C., 190° C. and 210° C. have equivalent quality, and the same for outlet air temperature of 90-100° C., 100-110° C. and 110-120° C.; and (3) all the spray dried powder has higher water content.

Example 4

Spray Drying Comparison of Vancomycin Concentrate of Different Concentrations with 25% Trehalose To 1600 mL of vancomycin concentrate (Batch No: 310121110, vancomycin B: 96.28%) with a vancomycin concentration of 15% (containing 240 g of vancomycin in total), added 60 g of trehalose (25% by weight of vancomycin), mixed well and concentrated through D200 nanofiltration membrane to 800 mL (30% vancomycin concentration), passed through 0.22 μm filter, then subdivided the obtained filtrate in quadruplicate, 200 mL each.

To these four portions, added 0 mL, 40 mL, 100 mL and 200 mL of purified water, respectively, mixed well to get solution A (30% vancomycin), B (25% vancomycin), C (20% vancomycin) and D (15% vancomycin).

Spray drying of solution A, B, C and D was performed using a drying gas having an inlet temperature of 190° C. and an outlet temperature of 100-110° C. Resultant powders were tested as shown in Table 6.

TABLE 5

Test results of spray dried powders of vancomycin Concentrate at different concentrations

| Test No. | 30% Conc. | 25% Conc. | 20% Conc. | 15% Conc. |
|---|---|---|---|---|
| Duration | 9:35-10:02 | 10:30-11:10 | 14:05-14:53 | 13:37-16:45 |
| Inlet Temperature (° C.) | 190 | 190 | 190 | 190 |
| Outlet Temperature (° C.) | 100-110 | 100-110 | 100-110 | 100-110 |
| Air volume (%) | 100 | 100 | 100 | 100 |
| Speed of pump (%) | 35 | 30 | 25 | 20 |
| Flow rate .of nitrogen (mm) | 50 | 50 | 50 | 50 |
| System pressure (mbar) | 15 | 15 | 15 | 15 |

TABLE 6

Test results of spray dried powder of different vancomycin concentrations

| Test No. | Original test | 30% Conc. | 25% Conc. | 20% Conc. | 15% Conc. |
|---|---|---|---|---|---|
| Moisture (%) | NA | 3.8 | 3.7 | 4.1 | 4.3 |
| pH, 5% Conc. | 2.81 | 2.89 | 2.81 | 2.81 | 22.82 |
| $A_{450}$, 10% Conc. | 0.054 | 0.057 | 0.057 | 0.052 | 0.052 |
| Vancomycin B (%) | 96.28 | 96.24 | 96.22 | 96.18 | 96.15 |
| Impurity $B_1$ (%) | 0.96 | 0.94 | 0.95 | 0.95 | 0.96 |
| Impurity $B_2$ (%) | 0.05 | 0.06 | 0.08 | 0.06 | 0.07 |
| Impurity $B_1$ and $B_2$ (%) | 1.01 | 1.00 | 1.03 | 1.01 | 1.03 |

*: Impurity B1: desamidovancomycin 1; Impurity B2: desamidovancomycin 2.

The results showed no significant quality difference for the spray dried vancomycin powders at different vancomycin concentrations. However, a higher vancomycin concentration can reduce drying time, reduce energy costs and increase efficiency.

Example 5

Spray Drying Study of 25% Vancomycin Concentrate with Different Amounts of Trehalose To 3000 mL of vancomycin concentrate (Batch No: 310121113, vancomycin B: 96.28%) with a vancomycin concentration of 10% (containing 300 g of vancomycin in total), subdivided the obtained filtrate in sextuplicate, 500 mL, each (50 g of vancomycin each).

To these six portions, added 2.5 g (5% by weight of vancomycin), 5 g (10% by weight of vancomycin), 7.5 g (15% by weight of vancomycin), 10 g (20% by weight of vancomycin), 12.5 g (25% by weight of vancomycin) and 15 g (30% by weight of vancomycin) of trehalose, respectively, mixed well and concentrated through D200 nano-filtration membrane to 200 mL, (25% vancomycin), then passed through 0.22 μm filter, collected the filtrates and marked as filtrate A, B, C, D, E and F, respectively.

Spray drying of filtrate A, B, C, D, E and F was performed using a drying gas having an inlet temperature of 190° C. and an outlet temperature of 100-110° C. The results of the experiments are shown below in Table 7 and 8.

TABLE 7

Spray drying data of vancomycin concentrate with different amount of trehalose

| Test. No. | Trehalose 5% (W/W) | Trehalose 10% (W/W) | Trehalose 15% (W/W) | Trehalose 20% (W/W) | Trehalose 25% (W/W) | Trehalose 30% (W/W) |
|---|---|---|---|---|---|---|
| Duration Start-stop | 8:33-9:12 | 9:30-10:04 | 10:36-11:17 | 13:32-14:05 | 14:35-14:59 | 15:30-16:01 |
| Inlet Temperature, ° C. | 190 | 190 | 190 | 190 | 1.90 | 190 |
| Outlet Temperature, ° C. | 100-110 | 100-110 | 100-110 | 100-110 | 100-110 | 100-110 |
| Air volume (%) | 100 | 100 | 100 | 100 | 100 | 100 |
| Speed of pump (%) | 20 | 25 | 25 | 30 | 30 | 35 |
| Flow rate of Nitrogen (mm) | 50 | 50 | 50 | 50 | 50 | 50 |
| System pressure (mbar) | 15 | 15 | 15 | 15 | 15 | 15 |

TABLE 8

Test results of spray dried powder of vancomycin concentration with different amount of trehalose

| Test. No. | Concentration | Trehalose 5% (W/W) | Trehalose 10% (W/W) | Trehalose 15% (W/W) | Trehalose 20% (W/W) | Trehalose 25% (W/W) | Trehalose 30% (W/W) |
|---|---|---|---|---|---|---|---|
| Moisture, % | NA | 4.2 | 3.7 | 3.4 | 3.5 | 3.8 | 3.6 |
| pH, 5% Conc. | 2.81 | 2.89 | 2.81 | 2.89 | 2.84 | 2.85 | 2.81 |
| $A_{450}$, 10% Conc. | 0.054 | 0.052 | 0.057 | 0.057 | 0.052 | 0.052 | 0.055 |
| Vancomycin B (%) | 96.28 | 96.09 | 96.14 | 96.13 | 96.24 | 96.12 | 96.22 |
| Impurity $B_1$ (%) | 0.96 | 0.93 | 0.94 | 0.94 | 0.94 | 0.94 | 0.95 |
| Impurity $B_2$ (%) | / | 0.11 | 0.08 | 0.06 | 0.06 | 0.05 | 0.03 |
| Impurity $B_1$ and $B_2$ (%) | 0.96 | 1.04 | 1.02 | 1.00 | 1.00 | 0.96 | 0.98 |

From the data provided in Table 8, it can be seen that the spray dried powder has a similar quality when the amount of trehalose is from 5% to 30%.

Example 6

Spray Drying Study of Vancomycin Concentrate with Different Amounts of Tween 80

To 2500 mL of vancomycin concentrate (Batch No: 310130102, vancomycin B: 96.08%) with a vancomycin concentration of 10% (containing 250 g of vancomycin), added 62.5 g of trehalose (25% by weight of vancomycin), concentrated through D200 nano-filtration membrane to 1000 mL with a concentration of 25%, subdivided solution in quintuplicate, 200 mL each (50 g of vancomycin each).

For these five portions, added 0 mL, 0.1 mL (0.005% by weight of vancomycin), 0.2 mL (0.01% by weight of vancomycin), 0.4 mL (0.02% by weight of vancomycin) and 1 mL (0.05% by weight of vancomycin) of 2.5% Tween 80 solution, respectively, mixed well and passed through 0.22 μm filter to obtain filtrate A, B, C, D and E, respectively.

Spray drying of filtrate A, B, C, D and E was performed using a drying gas having an inlet temperature of 190° C. and an outlet temperature of 100-110° C. The results of the experiments are shown below in Table 9 and 10.

Example 7

Spray Drying Comparison of Vancomycin Concentration with Trehalose and Tween 80 or Mannitol and PEG Subdivided 2000 mL of concentrate (batch No: 310130105, vancomycin B: 96.40%) with a 15% vancomycin concentration (containing 300 g of vancomycin in total) in duplicate, 150 g vancomycin each. To one of them, added 37.5 g of trehalose (25% by weight of vancomycin), dissolved and concentrated through D200 nano-filtration membrane to 600 mL, then added 0.6 mL of 2.5% tween-80 solution (0.01% of by weight vancomycin), mixed well and passed through 0.22 μm filter to get filtrate A. To the other one, added 30 g of mannitol (20% of vancomycin by weight) and 30 g of PEG-400 (20% of vancomycin by weight), mixed well, concentrated through D200 nano-filtration membrane to 600 mL, then passed through 0.22) μm filter, collected the filtrate and marked as filtrate B.

Subdivided filtrate A in triplicate, 200 mL each. Conducted spray drying respectively with an inlet temperature 190° C. and an outlet temperature of 100-110° C. and the obtained dried powder batches are 0204, 0205 and 0206,

TABLE 9

Spray drying data of vancomycin concentrate with different amount of Tween-80

| Test No. | Tween 80 0.00% | Tween 80 0.05% | Tween 80 0.02% | Tween .80 0.01% | Tween 80 0.005% |
|---|---|---|---|---|---|
| Duration Start-stop | 9:03-9:32 | 9:55-10:34 | 10:57-11:23 | 13:45-14:15 | 14:55-13:29 |
| Inlet Temperature, ° C. Outlet Temperature, ° C. | 190 100-110 | 190 100-110 | 190 100-110 | 190 100-110 | 190 100-110 |
| Air volume (%) | 100 | 100 | 100 | 100 | 100 |
| Speed of pump (%) | 20 | 25 | 25 | 30 | 30 |
| Flow rate of Nitrogen (mm) | 50 | 50 | 50 | 50 | 50 |
| System pressure (mbar) | 15 | 15 | 15 | 15 | 15 |

TABLE 10

Test results of spray dried vancomycin powder with different amount of Tween-80

| Test No. | Concentrate | Tween 80 0.00% | Tween 80 0.05% | Tween 80 0.02% | Tween 80 0.01% | Tween 80 0.005% |
|---|---|---|---|---|---|---|
| Moisture % | NA | 4.2 | 2.1 | 2.3 | 2.5 | 2.8 |
| pH, 5% Conc. | 2.85 | 2.89 | 2.84 | 2.87 | 2.85 | 2.85 |
| $A_{250}$, 10% Conc. | 0.052 | 0.057 | 0.057 | 0.056 | 0.055 | 0.053 |
| Vancomycin B (%) | 96.08 | 96.01 | 96.02 | 96.03 | 96.04 | 96.02 |
| Impurity $B_1$ (%) | 0.69 | 0.70 | 0.70 | 0.69 | 0.68 | 0.70 |
| Impurity $B_2$ (%). | / | 0.05 | 0.03 | 0.06 | / | / |
| Impurity $B_1$ and $B_2$ (%) | 0:69 | 0.75 | 0.73 | 0.75 | 0.68 | 0.70 |
| Reconstitution Time (Seconds, 5% Conc.)* | NA | 28 S | 15 S | 16 S | 14 S | 17 S |

*Reconstitution time of 5. % Conc. means the required time of totally dissolving of containing vancomycin hydrochloride 0.5 g sample in 10 mL WFI in 15 ml Vials.

From the data in Table 10, it can be concluded that: (1) the water content of spray dried powder decreases significantly when adding tween-80; and (2) the reconstitution time of spray dried powder becomes short when adding tween-80.

respectively. Conducted the same operations for filtration B and the obtained batches are 0201, 0202 and 0203, respectively. The results of the experiments are shown below in Table 11 and 12, respectively.

TABLE 11

Spray drying data of vancomycin concentrate with different formulations

| | Formulations Trehalose, 25% (W/W) Tween 80, 0.01% Vancomycin B, 74.99% | | | Formulations Mannitol, 20% (W/W) PEG400, 20% Vancomycin B, 60% | | |
|---|---|---|---|---|---|---|
| Test No. | 0204 | 0205 | 0206 | 0201 | 0202 | 0203 |
| Duration Start stop | 13:34-14:12 | 14:30-15.04 | 15:40-16:17 | 8:34-9:08 | 9:49-10:20 | 10:40-11:09 |
| Inlet Temp., °C. | 190 | 190 | 190 | 190 | 190 | 190 |
| Outlet Temp., °C. | 100-110 | 100-110 | 100-110 | 100-110 | 100-110 | 100-110 |
| Air volume (%) | 100 | 100 | 100 | 100 | 100 | 100 |
| Speed of pump (%) | 30 | 30 | 30 | 30 | 30 | 30 |
| Flow rate of Nitrogen (mm) | 50 | 50 | 50 | 50 | 50 | 50 |
| System pressure (mbar) | 15 | 15 | 15 | 15 | 15 | 15 |

TABLE 12

Test results of spray dried vancomycin powder with different formulations

| | | Formulations Trehalose, 25% (W/W) Tween 80, 0.01% Vancomycin B, 74.99% | | | Formulations Mannitol, 20% (W/W) PEG400, 20% Vancomycin B, 60% | | |
|---|---|---|---|---|---|---|---|
| Test No. | Concentrate | 0204 | 0205 | 0204 | 0205 | 0204 | 0205 |
| Moisture % | NA | 2.2 | 2.4 | 2.4 | 2.5 | 2.8 | 2.6 |
| pH, 10% Conc. | 3.05 | 3.11 | 3.14 | 3.10 | 3.15 | 3.13 | 3.11 |
| $A_{450}$, 10% Conc. | 0.056 | 0.052 | 0.054 | 0.055 | 0.062 | 0.054 | 0.053 |
| Vancomycin B (%) | 96.40 | 96.16 | 96.31 | 96.26 | 95.86 | 95.93 | 95.87 |
| Impurity $B_1$(%) | 0.55 | 0.54 | 0.52 | 0.55 | 0.70 | 0.71 | 0.72 |
| Impurity $B_2$ (%) | / | 0.07 | / | / | 0.07 | 0.07 | 0.07 |
| Impurity $B_1$ and $B_2$ (%) | 0.55 | 0.61 | 0.52 | 0.55 | 0.77 | 0.78 | 0.79 |
| Reconstitution Time (Seconds, 5% Conc.)* | NA | 15 | 17 | 16 | 23 | 25 | 22 |

*Reconstitution time of 5% Conc. means the required time of totally dissolving of containing vancomycin hydrochloride 0.5 g sample in 10 mL WFI in 15 ml Vials.

From the data in Table 12, it can be conclude that: (1) the spray dried vancomycin powder with the formulation of trehalose and tween 0.80 has higher vancomycin B and a lower level of impurity B; and (2) the spray dried vancomycin powder with the for mulation of trehalose and tween 80 has a shorter reconstitution time at a concentration of 5%.

Example 8

Stability Study of Spray Dried Vancomycin Powder with and without Excipients

Subdivided 1500 mL (containing 150 g of vancomycin in total) of concentrate (batch No: 310130208, vancomycin B: 96.40%) with a 10% vancomycin concentration in triplicate, 50 g of vancomycin and 500 mL each.

To one of them, added 12.5 g of trehalose (25% by weight of vancomycin), dissolved and concentrated through D200 nano-filtration membrane to 200 mL, then added 0.5 mL of 1.0% tween-80 solution (0.01% by weight of vancomycin), mixed well and passed through 0.22 μm filter to get filtrate A with a vancomycin concentration of 25%. Concentrated the other one through D200 nano-filtration membrane to 200 mL, then passed through 0.22 μm filter to get filtrate B with a vancomycin concentration of 25%. For the last one, added 10 g of mannitol (20% by weight of vancomycin), and 10 g of PEG-400 (20% by weight of vancomycin), dissolved and concentrated through D200 nano-filtration membrane, then passed through 0.22 μm filter to get filtrate C with a vancomycin concentration of 25%.

Conducted spray drying respectively with an inlet temperature 190° C. and an outlet temperature of 100-110° C. The results of the experiments are shown below in Tables 13 and 14, respectively.

Stored the spray dried powder in 60° C. chamber and tested the impurity level by HPLC periodically. The results are shown in Table 15.

TABLE 13

Spray drying data of vancomycin concentrate with and without excipients

| | Formulations | | |
|---|---|---|---|
| Test No. | Trehalose, Tween 80 Vancomycin | Vancomycin Without excipients | Mannitol PEG-400 Vancomycin |
| Duration Start-stop | 8:55-9:10 | 9:40-10:18 | 10:40-11:18 |
| Inlet Temperature, °C. | 190 | 190 | 190 |
| Outlet Temperature, °C. | 100-110 | 100-110 | 100-110 |
| Air flow (%) | 100 | 100 | 100 |
| Speed of pump (%) | 30 | 25 | 30 |

TABLE 13-continued

Spray drying data of vancomycin concentrate with and without excipients

| | Formulations | | |
|---|---|---|---|
| Test No. | Trehalose, Tween 80 Vancomycin | Vancomycin Without excipients | Mannitol PEG-400 Vancomycin |
| Flow rate of Nitrogen (mm) | 50 | 50 | 50 |
| System pressure (mbar) | 15 | 15 | 15 |

TABLE 14

Product results of spray dried vancomycin powder with and without excipients

| Test No. | Trehalose, Tween 80 Vancomycin | Vancomycin Without excipients | Mannitol PEG-400 Vancomycin |
|---|---|---|---|
| Moisture, % | 2.8 | 4.7 | 2.7 |
| pH, 5% Conc. | 2.95 | 2.91 | 2.91 |
| $A_{450}$, 10% Conc. | 0.052 | 0.057 | 0.053 |
| Vancomycin B (%) | 96.16 | 95.58 | 95.80 |
| Impurity $B_1$ (%) | 0.54 | 0.57 | 0.70 |
| Impurity $B_2$ (%) | 0.07 | 0.13 | 0.07 |
| Impurity $B_1$ and $B_2$ (%) | 0.61 | 0.70 | 0.77 |
| Reconstitution Time (Seconds, 5% Conc.)* | 15 S | 24 S | 14 S |

*Reconstitution time of 5% Conc. means the required time of totally dissolving of containing vancomycin hydrochloride 0.5 g sample in 10 mL WFI in 15 ml Vials.

TABLE 15

Stability study of spray dried vancomycin powder with and without excipients

| Test No. | Day 1, 60° C. | Day 2, 60° C. | Day 3, 60° C. | Day 5, 60° C. |
|---|---|---|---|---|
| Trehalose and tween 80 | | | | |
| Vancomycin B (%) | 95.76 | 95.35 | 94.95 | 94.48 |
| Impurity $B_1$ (%) | 0.82 | 0.85 | 1.08 | 1.25 |
| Impurity $B_2$ (%) | 0.08 | 0.17 | 0.25 | 0.29 |
| Impurity $B_1$ and $B_2$ (%) | 0.90 | 1.02 | 1.33 | 1.54 |
| Without excipient | | | | |
| Vancomycin B (%) | 93.64 | 92.82 | 93.36 | 90.82 |
| Impurity $B_1$ (%) | 0.93 | 1.18 | 1.30 | 1.76 |
| Impurity $B_2$ (%) | 0.46 | 0.64 | 0.71 | 1.00 |
| Impurity $B_1$ and $B_2$ (%) | 1.39 | 1.82 | 2.01 | 2.76 |
| Mannitol and PEG | | | | |
| Vancomycin B (%) | 95.08 | 94.48 | 93.94 | 93.31 |
| Impurity $B_1$ (%) | 0.88 | 1.33 | 1.37 | 1.73 |
| impurity $B_2$ (%) | 0.11 | 0.16 | 0.17 | 0.20 |
| Impurity $B_1$ and $B_2$ (%) | 0.99 | 1.49 | 1.54 | 1.93 |

Figure 6:
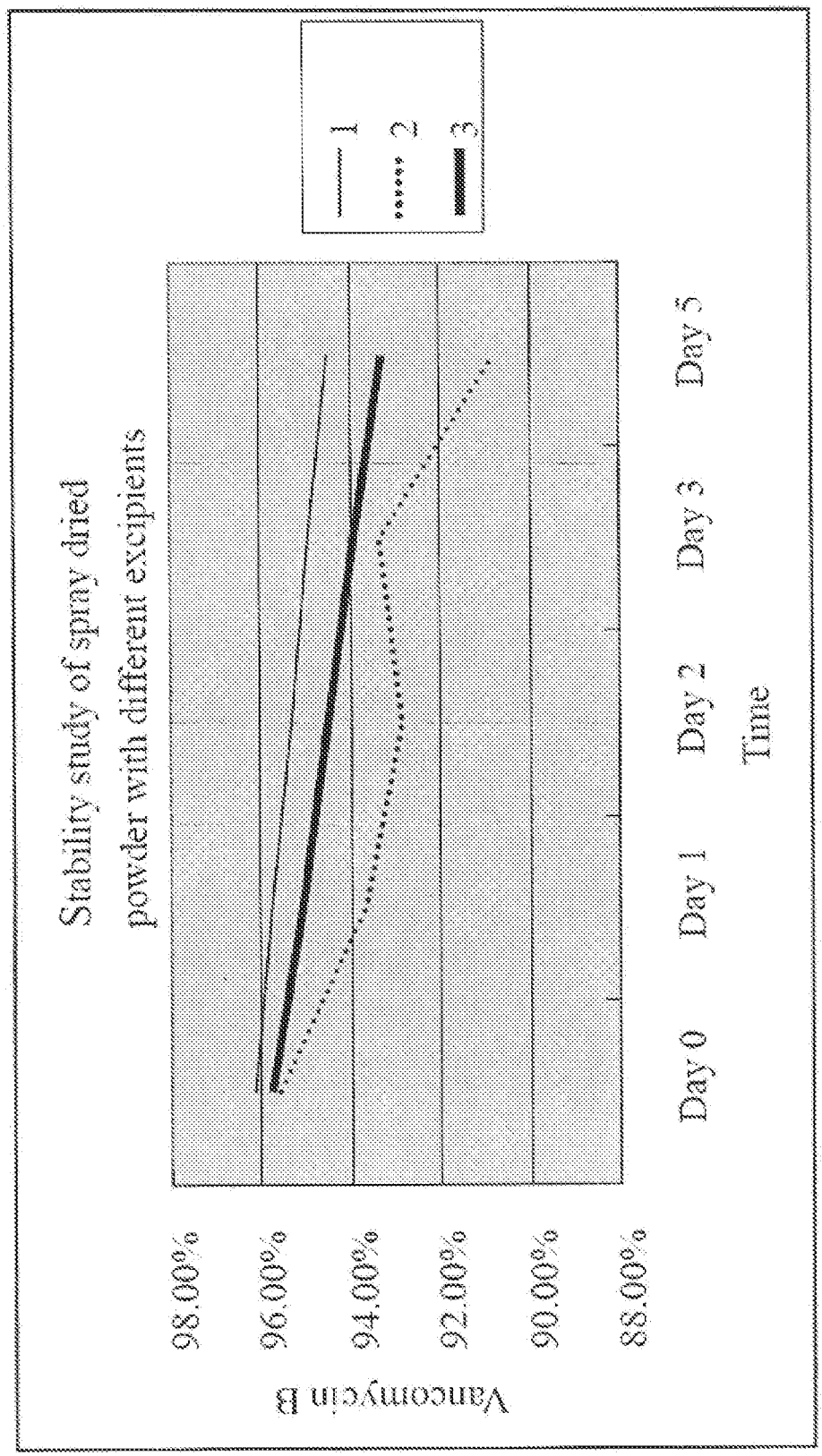
FIG. 6 shows a vancomycin B versus time diagram that illustrates a stability study of spray dried powder with different excipients.

FIG. 6 shows a vancomycin B versus time diagram that illustrates the results of the stability study of the spray dried powder with different excipients. In the diagram, curve 1 denotes spray dried powder with trehalose and tween 80, curve 2 denotes spray dried powder without excipient, and curve 3 denotes spray dried powder with mannitol and PEG-400.

From the data in Table 15, it can be seen that the formulation with trehalose and tween has the best product stability, followed by the formulation of mannitol and PEG. Vancomycin without excipients has the worst stability.

Example 9

Spray Drying Study of Vancomycin Concentrate at Different Concentrations

To 1800 mL (containing 180 g of vancomycin in total) of vancomycin concentrate (batch No: 310130210, vancomycin B: 96.05%) with a 10% vancomycin concentration, added 45 g of trehalose (25% by weight of vancomycin), dissolved and concentrated through D200 nano-filtration membrane to 600 mL, then added 1.8 mL of 1.0% tween-80 solution (0.01% by weight of vancomycin), mixed well and passed through 0.22 μm filter. Subdivided the obtained filtrate in triplicate, 200 mL each (containing 60 g of vancomycin each). Added 40 mL, 100 mL and 0 mL of purified water, respectively, mixed well to get solution A (25% vancomycin), B (20% vancomycin) and C (30% vancomycin).

Spray drying of solution A, B and C were performed with an inlet temperature of 190° C. and an outlet temperature of 100-110° C. The results of the experiments are shown below in Tables 16 and 17, respectively.

TABLE 16

Spray drying data of vancomycin concentrate at different concentrations

| Test No. | 30% Conc. | 25% Conc. | 20% Conc. |
|---|---|---|---|
| Duration Start-stop | 14:15-14:46 | 15:10-15:55 | 16:35-17:35 |
| Inlet Temperature, ° C. | 190 | 190 | 190 |
| Outlet Temperature, ° C. | 100-110 | 100-110 | 100-110 |
| Air volume (%) | 100 | 100 | 100 |
| Speed of pump (%) | 30 | 30 | 25 |
| Flow rate of Nitrogen (mm) | 50 | 50 | 50 |
| System pressure (mbar) | 15 | 15 | 15 |

TABLE 17

Test results of spray dried vancomycin powder

| Test No. | Concentrate | 30% Conc. | 25% Conc. | 20% Conc. |
|---|---|---|---|---|
| Moisture, % | NA | 2.8 | 2.7 | 3.1 |
| pH, 5% Conc. | 3.05 | 3.14 | 3.11 | 3.16 |
| $A_{450}$, 10% Conc. | 0.046 | 0.052 | 0.047 | 0.051 |
| Vancomycin B (%) | 96.05 | 96.01 | 95.91 | 95.92 |
| Impurity $B_1$ (%) | 0.67 | 0.63 | 0.64 | 0.64 |
| Impurity $B_2$ (%) | / | / | / | / |
| Impurity $B_1$ and $B_2$ (%) | 0.67 | 0.63 | 0.64 | 0.64 |
| Reconstitution Time (Seconds, 5% Conc.)* | NA | 17 | 14 | 15 |

*Reconstitution time of 5% Conc. means the required time of totally dissolving of containing vancomycin hydrochloride 0.5 g sample in 10 mL WFI in 15 ml Vials.

From the data in Table 17, it can be seen that the spray dried powder obtained by vancomycin solutions with different concentrations 20%, 25% and 30% has similar quality.

Example 10

Spray Drying of Vancomycin Concentrate with Different Formulations

To 3500 mL (containing 350 g of vancomycin in total) of vancomycin concentrate (batch No: 310130208, vancomycin B: 96.40%) with a 10% vancomycin concentration, added 87.5 g of trehalose (25% by weight of vancomycin), dissolved and concentrated through D200 nano-filtration membrane to 1400 mL, subdivided the obtained filtrate in septuplicate, 200 mL each (containing 50 g of vancomycin each).

To six of them, added 0.5 ml of 1.0% tween-80 solution (0.01% by weight of vancomycin), 2.5 ml of 1.0% poloxamer 188 (0.05% by weight of vancomycin), 2.5 ml of 1.0% polyethylene glycol (0.05% by weight of vancomycin), 2.5 ml of 1.0% castor oil hydrogenated (0.05% by weight of vancomycin), 2.5 ml of 1.0% polyglycol 12 hydroxystearate (0.05% by weight of vancomycin), and 2.5 ml of 1.0% polyoxyethylene castor oil hydrogenated, respectively, mixed well and passed through 0.22 μm filter, collected the filtrate and marked as filtrate A, C, D, E, F and G, respectively. Each one has a vancomycin concentration of 25%.

To the last one, passed through 0.22 μm filter, collected the filtrate and marked as filtrate B.

Spray drying of solution A, B, C, D, E, F and G were performed with an inlet temperature of 190° C. and an outlet temperature of 100-110° C. The results of the experiments are shown below in Table 18.

TABLE 18

Test results of spray dried vancomycin powder

| Test. No. | Moisture, % | Reconstitution Time (Seconds, 5% Conc.)* | pH, 5% Conc. |
|---|---|---|---|
| Tween-80 | 2.1 | 14 | 2.92 |
| Blank | 3.9 | 29 | 2.91 |
| Poloxamer 188 | 2.8 | 21 | 2.93 |
| Polyethylene glycol | 3.0 | 19 | 2.92 |
| Castor oil hydrogenated | 3.1 | 19 | 2.91 |
| Polyglycol 12 hydroxystearate | 3.2 | 22 | 2.93 |
| Polyoxyethylene castor oil Hydrogenated | 2.6 | 18 | 2.95 |

*Reconstitution time of 5% Conc. means the required time of totally dissolving of containing vancomycin hydrochloride 0.5 g sample in 10 mL WFI in 15 ml Vials.

From the data in table 18, it can be concluded that spray dried powder with excipients, preferably tween-80, has a faster dissolving rate.

The above examples are meant to be illustrative of the disclosure and do not limit the disclosure. It will be readily apparent to those of ordinary skill in the art that certain changes and modifications may be made thereto without departing from the spirit or scope of the appended claims.

The terms "including," "comprising" and variations thereof, as used in this disclosure, mean "including, but not limited to," unless expressly specified otherwise.

The terms "a," "an," and "the," as used in this disclosure, means "one or more," unless expressly specified otherwise.

Devices that are in communication with each other need not be in continuous communication with each other, unless expressly specified otherwise. In addition, devices that are in communication with each other may communicate directly or indirectly through one or more intermediaries.

Although process steps, method steps, algorithms, or the like, may be described in a sequential order, such processes, methods and algorithms may be configured to work in alternate orders. It is noted that all process steps disclosed herein may be carried out aseptically. In other words, any sequence or order of steps that may be described does not necessarily indicate a requirement that the steps be performed in that order. The steps of the processes, methods or algorithms described herein may be performed in any order practical. Further, some steps may be performed simultaneously.

When a single device or article is described herein, it will be readily apparent that more than one device or article may be used in place of a single device or article. Similarly, where more than one device or article is described herein, it will be readily apparent that a single device or article may be used in place of the more than one device or article. The functionality or the features of a device may be alternatively embodied by one or more other devices which are not explicitly described as having such functionality or features.

What is claimed is:

1. A method for preparing spray dried powder comprising vancomycin hydrochloride, the method comprising the steps of:

(1) providing a vancomycin hydrochloride solution with a chromatographic purity of at least 95%;

(2) adding trehalose in an amount of about 5-35% by weight of dry vancomycin hydrochloride and a solubilizer in an amount of about 0.005-0.05% by weight of dry vancomycin hydrochloride to the solution of Step (1), to form a mixture solution of the vancomycin hydrochloride;

(3) concentrating the mixture solution of the vancomycin hydrochloride of Step (2) by a membrane concentration device to form from about 20% to about 30% vancomycin hydrochloride concentrate;

(4) filtering the vancomycin hydrochloride concentrate of Step (3) to form a vancomycin hydrochloride filtrate; and (5) spray drying the vancomycin hydrochloride filtrate of Step (4) to form a spray dried vancomycin hydrochloride powder with EP impurity B level of not more than 1.5%.

2. The method of claim 1, wherein the vancomycin hydrochloride concentrate has a pH of about 2.0-4.0.

3. The method of claim 1, wherein the vancomycin hydrochloride solution with the chromatographic purity of at least 95% is prepared by dissolving a vancomycin hydrochloride active pharmaceutical ingredient in purified water or in water for injection.

4. The method of claim 1, wherein Step (1) comprises: preparing a fermentation solution by culturing *Amycolatopsis oriertalis* under suitable conditions for 4-6 days to obtain a broth containing vancomycin, and then obtaining the vancomycin hydrochloride concentrate from said broth by way of a series of steps comprising filtration, resin adsorption, discoloring, concentrating, crystallizing, dissolving, chromatographic separating, adjusting pH, filtrating, and concentrating.

5. The method of claim 1, wherein a weight ratio of trehalose to the vancomycin hydrochloride is about 20-25%.

6. The method of claim 1, wherein the solubilizer is polyoxyethylene sorbitan monooleate (tween 80), poloxamer 188, polyethylene glycol (35), castor oil hydrogenated (RH-35), polyethylene glycol (40), castor oil hydrogenated (RH-40), or polyglycol-12-hydroxystearate.

7. The method of claim 6, wherein the solubilizer is polyoxyethylene sorbitan monooleate, and the weight ratio of polyoxyethylene sorbitan monooleate to the dry vancomycin hydrochloride is 0.01%.

8. The method of claim 5, wherein the solubilizer is polyoxyethylene sorbitan monooleate (tween 80), poloxamer 188, polyethylene glycol (35), castor oil hydrogenated (RH-35), polyethylene glycol (40), castor oil hydrogenated (RH-40), or polyglycol-12-hydroxystearate.

9. The method of claim 8, wherein the solubilizer is polyoxyethylene sorbitan monooleate, and the weight ratio of polyoxyethylene sorbitan monooleate to the dry vancomycin hydrochloride is 0.01%.

10. The method of claim 1, wherein a membrane of the membrane concentration device is a reverse osmosis membrane or a 200-800 Da nano-filtration membrane; and the temperature during concentrating does not exceed 20° C.

11. The method of claim 1, wherein when initiating a spray drier and heating device during the spray drying step of Step (5), the inlet temperature is controlled from about 160° C. to about 240° C., and the outlet temperature is controlled from about 80° C. to about 120° C. by opening a feeding switch to keep system at a positive pressure state and providing a heating carrier that is more than 95% nitrogen.

12. The method of claim 1, wherein the spray dried vancomycin hydrochloride powder has a water content below 3%.

13. The method of claim 1, wherein the spray dried vancomycin hydrochloride powder is sterile.

14. The method of claim 13, which further comprises: filling a vial with the sterile spray dried vancomycin hydrochloride powder in a dosage form by a sterile filling device; sealing the vial while under a nitrogen gas atmosphere to provide a sealed dosage form, wherein the sealed dosage form comprises a dosage strength of about 0.5 g, about 0.75 g, about 1.0 g, about 2 g, about 5 g, about 10 g or about 20 g.

15. The method of claim 2, wherein the vancomycin hydrochloride concentrate is stored at a temperature of about 2-8° C. for not more than about 120 hours.

16. The method of claim 13, wherein the sterile vancomycin hydrochloride is administered orally or intravenously.

17. The method of claim 14, wherein the sterile vancomycin hydrochloride is administered orally or intravenously.

* * * * *